(12) United States Patent
Xue et al.

(10) Patent No.: US 8,653,048 B2
(45) Date of Patent: Feb. 18, 2014

(54) PRODRUGS BASED ON GEMCITABINE STRUCTURE AND SYNTHETIC METHODS AND APPLICATIONS THEREOF

(75) Inventors: Xiaoxia Xue, Jining (CN); Gang Li, Jinan (CN); Changjun Sun, Jinan (CN); Wenbao Li, Jinan (CN)

(73) Assignee: Sanlugen Pharmatech Ltd., Jinan (CN)

( * ) Notice: Subject to any disclaimer, the term of this patent is extended or adjusted under 35 U.S.C. 154(b) by 138 days.

(21) Appl. No.: 13/265,335

(22) PCT Filed: Mar. 25, 2010

(86) PCT No.: PCT/CN2010/000372
§ 371 (c)(1),
(2), (4) Date: Dec. 15, 2011

(87) PCT Pub. No.: WO2010/121486
PCT Pub. Date: Oct. 28, 2010

(65) Prior Publication Data
US 2012/0088908 A1    Apr. 12, 2012

(30) Foreign Application Priority Data
Apr. 21, 2009    (CN) .......................... 2009 1 0020716

(51) Int. Cl.
*A61K 31/70*    (2006.01)
*C07H 19/00*    (2006.01)

(52) U.S. Cl.
USPC .......................... 514/49; 536/28.2; 536/28.51

(58) Field of Classification Search
None
See application file for complete search history.

(56) References Cited

U.S. PATENT DOCUMENTS

| 2005/0101775 A1 | 5/2005 | Erion et al. |
| 2007/0225248 A1 | 9/2007 | Myhren et al. |

FOREIGN PATENT DOCUMENTS

| CN | 101525361 A | 9/2009 |
| WO | WO9832762 A1 | 7/1998 |
| WO | 2004/041203 A2 | 5/2003 |
| WO | WO2004/041203 * | 5/2004 |
| WO | WO2005025552 A2 | 3/2005 |
| WO | WO2006030217 A2 | 3/2006 |
| WO | WO2006/065525 * | 6/2006 |
| WO | WO2006065525 A1 | 6/2006 |
| WO | WO2006098628 A1 | 9/2006 |
| WO | WO2007149891 A2 | 12/2007 |
| WO | WO2009053654 A2 | 4/2009 |

OTHER PUBLICATIONS

International Search Report and Written Opinion issued by the International Search Authority (Chinese Patent Office) for PCT Application No. PCT/CN2010/000372 on Jun. 24, 2010.
Erion et al., "Design, Synthesis, and Characterization of a Series of Cytochrome P450 3A-Activated Prodrugs (HepDirect Prodrugs) Useful for Targeting Phosph(on)ate-Based Drugs to the Liver" J. Am. Chem. Soc. 2004, 126 (16): 5154-5163.
Rooseboom et al., "Enzyme-Catalyzed Activation of Anticancer Prodrugs" Pharmacol Rev 56 (1): 53-102 (2004).
Song et al., "Amino Acid Ester Prodrugs of the Anticancer Agent Gemcitabine: Synthesis, Bioconversion, Metabolic Bioevasion, and hPEPT1-Mediated Transport" Molecular Pharmaceutics. 2 (2): 157-167 (2005).
Wu et al., "Synthesis and Biological Activity of a Gemcitabine Phosphoramidate Prodrug" J Med. Chem. Author manuscript; available in PMC Aug. 20, 2008.

* cited by examiner

*Primary Examiner* — Traviss C McIntosh, III
(74) *Attorney, Agent, or Firm* — Jun He Law Office P.C.; Zhaohui Wang

(57) ABSTRACT

Prodrugs based on gemcitabine structure shown in formula (I) as well as their synthetic method and application are disclosed in the present invention, wherein the definitions for the groups of a, b, c, d, E, Z and V are described in the specification. By modifying the $N^4$ group, the solubility, the bioavailability and the organ specificity of the prodrugs are improved. Therefore, the fast metabolism problem is overcome for the produced prodrugs compounds. Intestinal toxicity induced by gemcitabine is decreased. Thereby, the prodrugs can be delivered by oral administration in clinics and further improve their anti-tumor, anti-cancer, anti-infection and diffusion preventing capability, and can also specifically act on liver or colon. The synthetic method is simple and adapted to industrial production.

10 Claims, No Drawings

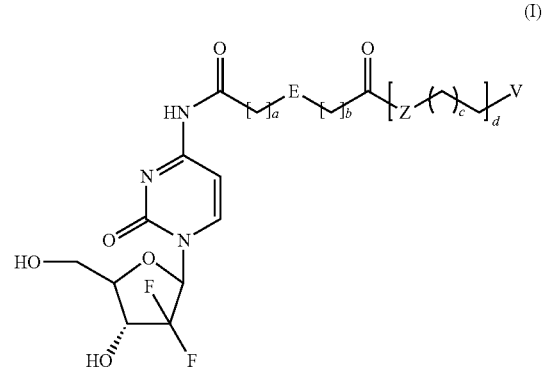

(I)

PRODRUGS BASED ON GEMCITABINE STRUCTURE AND SYNTHETIC METHODS AND APPLICATIONS THEREOF

FIELD OF THE INVENTION

The present invention belongs to the field of nucleoside drugs, particularly relates to prodrugs based on the structure of gemcitabine and synthetic methods and applications for treating cancer and other relevant diseases thereof.

BACKGROUND

According to the statistics of WHO, newly diagnosed cancer patients worldwide were as many as 12 million in 2007 and over 7 million cancer patients died every year around the world. This number was very close to the number for death from acute angiocardiopathy. Cancer is going to be the disease that leads to the most death in the world.

Nucleoside drugs, such as cytarabine, gemcitabine, decitabine, azacitidine, cladribine, fludalabine, atromide, nelarabine, 6-azauridine and tiazofurine have been widely used in the treatment for various cancers. Meanwhile many nucleoside drugs are in the clinical stage, for instance, 4'-thiofluoro-ara-C, 2'-deoxo-2'-fluoromethylcytidine, 4'-thio-ara-C and 3'-ethynylcytidine (ECYD).

Gemcitabine hydrochloride the chemical name of which is 2-Deoxy-2,2-difluorocytidine hydrochloride is a nucleoside drug. It was developed by Eli Lilly and was approved to go on the market of Australia and Finland in 1995 with the trade name of Gemzar (Chinese trade name: Jian Ze). Gemcitabine hydrochloride is a cell cycle specific antimetabolite drug. It mainly acts on cancer cells in the DNA synthesis phase, i.e. S-phase cells. Under certain conditions, it prevents cells in G1 phase from entering into S phase. As a prodrug, gemcitabine hydrochloride is an excellent substrate of thymine deoxyriboside kinase phosphorylation. In the presence of an enzyme, it is changed to gemcitabine monophosphate (dFdCMP), gemcitabine diphosphate (dFdCDP) and gemcitabine triphosphate (dFdCTP). Both dFdCDP and dFdCTP are the active products. dFdCDP inhibits ribonucleotide reductase, thereby reduces the amount of deoxynucleotide which is necessary for DNA repair. Gemcitabine hydrochloride is effective for treating non-small cell lung cancer, pancreatic cancer, bladder cancer, breast cancer or other solid tumors. In clinics, gemcitabine has to be administrated by intravenous injection rather than oral administration due to its intestinal toxicity and low bioavailability.

5-FU (5-Fluorouracil) is a basic drug for the treatment of late-stage colorectal cancer Gemcitabine hydrochloride can facilitate binding of 5-FU to its target (thymidylate synthetase), enhancing the inhibiting effect of the latter on DNA synthesis. Colon cancer is a colon malignant epithelial tumor. It is one of the most common malignant tumors in Europe, North America and Australian. Colon cancer is the second cancer cause of death. Although the morbidity rate of colon cancer was lower in African, Asia, South America, the morbidity rate is rising as the life style is changed to western style.

However, gemcitabine hydrochloride cannot be used to treat liver cancer, because it becomes inactive quickly in liver.

Liver cancer is the third leading cancer cause of death in the world. The risk factors include HBV or HCV. It was known that the 60%-80% of Hepatocellular Carcinoma were provoked by HBV. Because of the lack of efficacious chemotherapeutic agent, there is no standard treatment for liver cancer until today. It was reported that doxorubicin was the most widely used drug, but its action was supported only by one randomized controlled trial containing 60 patients. The fatal rate of complication provoked by Doxorubicin was nearly 25%. Mitoxantrone was approved to treat Hepatocellular Carcinoma; but it is not considered as an efficacy drug for treating liver cancer.

The clinical trials results of sorafenib, the evaluation project for drugs for liver cell cancer (SHARP), reported in the 43th American Society of Clinical Oncology (2007) made a big stir. The research results indicated that sorafenib was the first drug that could prolong the life of hepatocellular carcinoma patients at late-stage. The results may change the history of the primary standard treatment for late-stage hepatocellular carcinoma.

Due to the specificity of liver function, nucleoside drugs are metabolized quickly to inactive substances in liver and lose their activities. Up to today, there is not a nucleoside drug that can be used to treat hepatocellular carcinoma. Metabasis, a U.S. company, has developed a technique of direct enzymolysis in liver, i.e. enzymatic digestion of cyclic phosphate prodrugs in liver. It has been successfully used to clinical studies of noncyclic and cyclic antiviral and anticancer nucleoside compounds. The clinical assessment of the prodrug based on cytarabine for liver cancer is in progress (US2005/0101775; Mark Eron et al., *J. Am. Chem. Soc.* 2004, 126, 5154-5163). However, the work of Metabasis was only limited to the cyclic phosphorylation of cytarabine on the $O^5$ position.

The liver targeted nucleoside prodrugs have the following features:

(a). Specificity to liver, and it can be used to treat liver cancer in a targeted therapy.

(b). Accelerate the controlling steps of the phosphorylation in vivo, and increase its effect.

(c). Improved physicochemical properties, such as absorption, penetration, stability and pike performance.

(d). Reduce the side effect of nucleoside drugs without additional toxicity.

Due to common drug resistance of cancer cells and patients' urgent needs to new anti-cancer drugs, it is extremely urgent to develop new safe and reliable anti-cancer drugs from different angles to improve human health. The nucleoside prodrugs with organ specificity are one of the most promising new methods.

The nucleoside prodrugs are most promising new methods to reduce the side effect of anti-cancer drugs. The prodrugs of anti-cancer drugs are converted to active compounds when they are delivered to organ. The prodrugs of capecitabine and enocitabine etc. have been developed to overcome the defects of the nucleoside drugs. Now a lot of pharmaceutical companies are still working in developing methods for treating cancers by using other prodrugs (G. Xu, H. L. McLeod, Clin. Cancer Res., 2001, 7, 3314-3324; M. Rooseboom, J. N. M. Commandeur, N. P. E. Vermeulen, Pharmacol. Rev., 2004, 56, 53-102; W. D. Wu, J. Sigmond, G. J. Peters, R. F. Borch, J. Med. Chem. 2007, 50, 3743-3746).

The patents WO2005025552 and WO2006030217 have reported the synthesis of a series of prodrugs where the 5'-OH of gemcitabine ring was protected by carboxylic esters. Among them, there were monocarboxylic acid ester groups and biscarboxylic acid ester groups. The general formula was V-(L)$_n$-COO-(L)$_m$-D, V-(L)$_n$-COO-(L)$_P$-COO-(L)$_m$-D, wherein D was an active pharmaceutical ingredient, n, m, p was 0 or 1. L represented C$_{1-20}$ carbon chain, preferably 1-10, and more preferably 1-3. L represented (CH$_2$)$_q$, q was 1-3, or more than 3. V represented the terminal residue of the protect chain. V could be the groups or the atoms that were cleavable in metabolic process. Song et al. has reported that the 5'-OH of the gemcitabine ring was protected by amino acid ester groups (Song, X. et al. Mol Pharmaceutics 2004, 2, 157-167). Wu et al. has reported that the 5'-OH of the gemcitabine ring was protected by phosphate-amide groups (W. D. Wu, J. Sigmond, G. J. Peters, R. F. Borch, J. Med. Chem. 2007, 50, 3743-3746); Recently, WO2009/053654 has reported that the 5-OH of the gemcitabine ring was protected by phosphate-ester groups. The patents, WO98/32762, WO04/041203, WO2006098628 and US2007225248 have reported the simultaneous protection of the $O^5$ and the $N^4$ by saturated and unsaturated carboxylic esters and have conducted biological experiments.

Recently, LY2334737 a $N^4$ prodrug of gemcitabine protected by branched chain carboxylic acid amino group has been reported by Eli Lilly (WO2006/065525, WO2007/149891, Bender, et al. J. Med. Chem. 2009, 52, 6958-6961). It is in clinical trial, but the side effect of intestine toxicity has not been fully resolved yet.

Up to today, there is no patent and literature that report the protection of the $N^4$ position of gemcitabine by cyclodicarboxylic acid groups, including ester groups, amide groups, carboxylic groups and so on.

DISCLOSURE OF THE INVENTION

In view of the problems in existing technology, the purpose of the present invention is to provide prodrugs based on the structure of gemcitabine and methods of preparing the prodrugs based on the structure of gemcitabine. The gemcitabine of the present invention is used as the base structure of the prodrugs of the nucleoside anti-cancer drugs. In one aspect, the prodrugs are designed to overcome possible drug resistance in lung cancer cells and pancreatic cancer cells. On the other hand, its solubility, bioavailability and organ specificity are enhanced through modifying the $N^4$ position. The prodrugs can overcome the defect of fast-metabolism, reduce the toxicity of intestines caused by gemcitabine, improve its bioavailability, and make it possible for oral administration in clinics.

The present invention provides prodrugs based on a gemcitabine structure. The general structure formula of the prodrugs is shown as Formula (I)

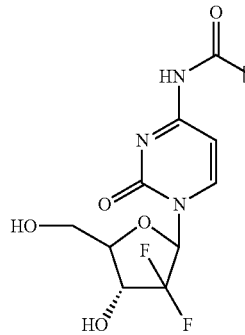

(I)

wherein a is an integer from 0 to 6; b is an integer from 0 to 6; c is an integer from 1 to 18; d is an integer from 1 to 4;

E is a 5-member or 6-member cyclic hydrocarbonyl, 5-member or 6-member cycloalkyl with 1-4 heteroatoms, aryl, or hetero-aryl. The heteroatoms are selected from O, N or S;

The connecting position in the ring can be any position that is chemically allowed. The rings may have no substitution, or have one or more substitutions which can be at any chemically allowed position of the ring.

Z is selected from O, N or S;

V is selected from hydrogen, alkyl, alkoxyl, ester group, halogen, amide group, amino or substituted amino.

Preferably, E is selected from one of the following structures:

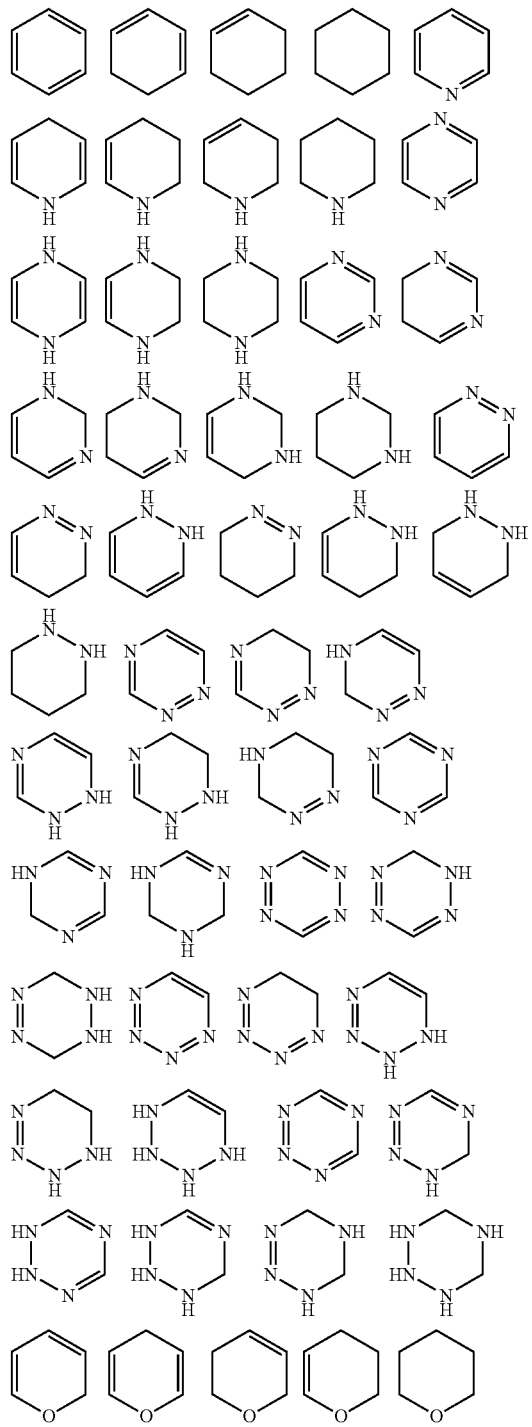

-continued

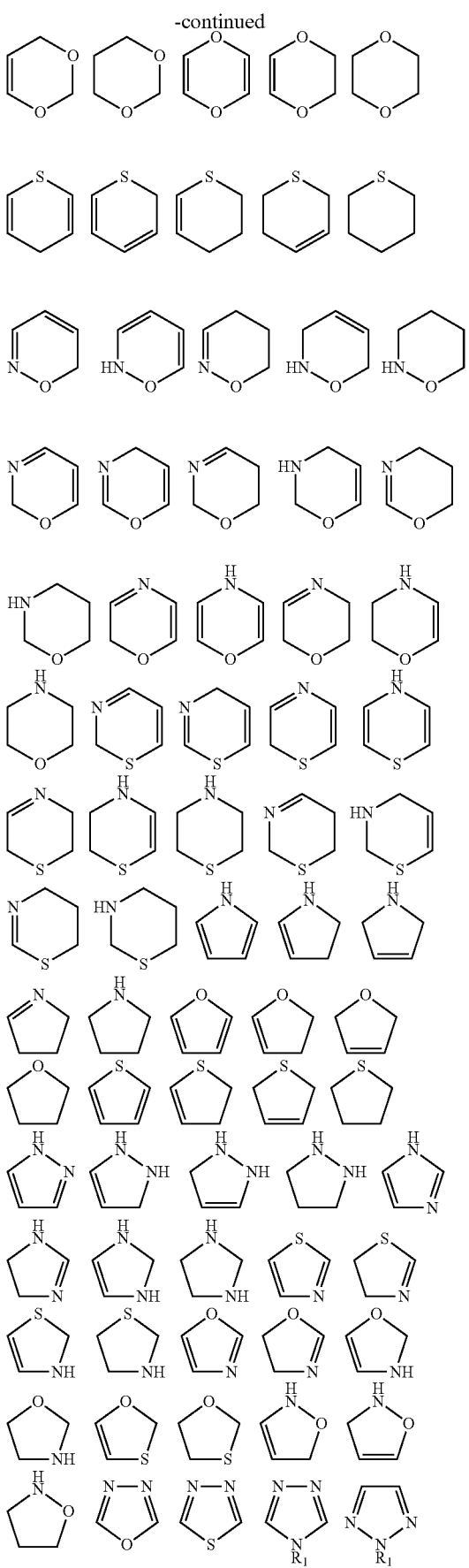

More preferably, E is selected from one of the following structures:

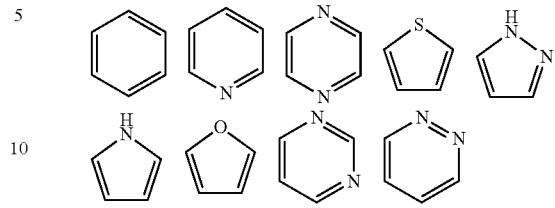

Preferably, a is 0 or 1; b is 0 or 1; Z is O or N; c is 10 to 16; d is 1 or 2;

Preferably, V is selected from hydrogen or alkyl. The representative synthesis route of gemcitabine prodrug derivatives is shown as follows:

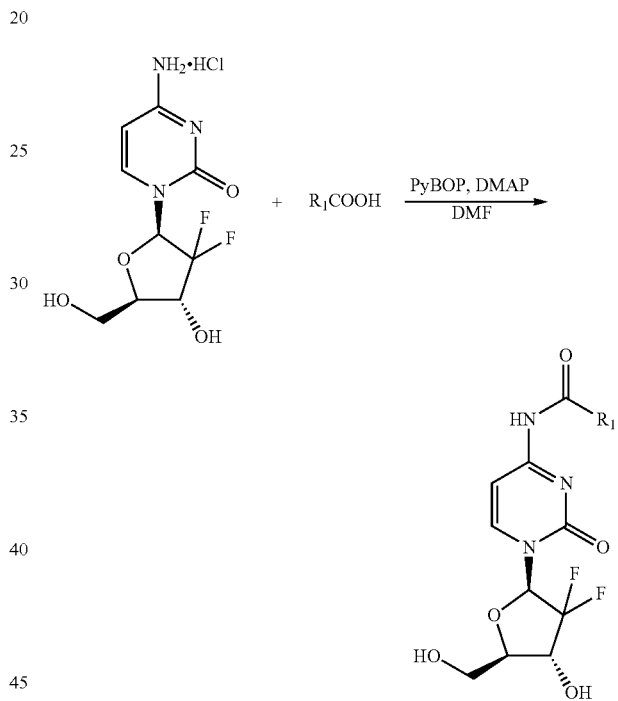

Wherein

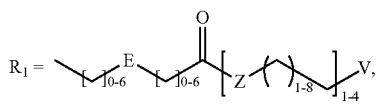

E, Z, V are as defined above.

The present invention also provides synthesis methods of these prodrugs based on the structure of gemcitabine. The methods include the following steps:

1) Acid anhydrides or acyl chlorides are mixed directly with alcohols or amines or dissolved in organic solvents with alcohols or amines at the mole ratio of acid anhydride or acyl chloride to alcohol or amine at 1:1-1:1.5, and react for 2-8 hours at any temperature ranging from room temperature to the reactants melting temperature to obtain the corresponding substituted acids;

2) Gemcitabine hydrochloride, the substituted acids obtained from step 1), benzotriazole-1-yl-oxytripyrrolidinylphosphonium hexafluorophosphate and 4-dimethylaminopyridine are dissolved in organic solvent at the mole ratio of 1:(1-2):(0.9-1.5):(1-3), and are stirred for 12-24 h at room temperature;

3) The reaction solution of step 2) is poured into water, and extracted. The extracted organic phase is dried and purified to produce the desired product.

Preferably, the acid anhydrides in step 1) are selected from phthalic anhydride, homophthalic anhydride, cyclohexane-1,2-dicarboxylic anhydride, cyclopentane-1,2-dicarboxylic anhydride, pyrazinedicarboxylic anhydride, pyridinedicarboxylic anhydride, thiophenedicarboxylic anhydride, furandicarboxylic anhydride, pyrroledicarboxylic anhydride, or 1,2,3,6-tetrahydrophthalic anhydride.

Preferably, the alcohols in step 1) are selected from methanol, n-octyl alcohol, n-nonyl alcohol, n-decyl alcohol, n-undecyl alcohol, lauryl alcohol, n-tetradecanol, n-hexadecanol, or n-octadecanol.

Preferably, the amines in step 1) are selected from n-octylamine, n-nonylamine, n-decylamine, n-undecylamine, n-laurylamine, n-tetradecylamine, n-hexadecylamine or n-octadecylamine.

Preferably, the organic solvents in step 1) or 2) are selected from N,N-dimethylformamide, N,N-dimethyl acetamide, tetrahydrofuran, dioxin, dimethyl sulfoxide, sulfolane or pyridine.

Preferably, the acyl chlorides in step 1) are obtained by reaction of dicarboxylic acids with $SOCl_2$, $PCl_5$, $PCl_3$ or $POCl_3$. The dicarboxylic acids in step 1) are selected from pyrazine-2,3-dicarboxylic acid, pyridazine-3,6-dicarboxylic acid, isophthalic acid, pyrimidine-4,6-dicarboxylic acid, pyridine-2,5-dicarboxylic acid, pyridine-2,3-dicarboxylic acid, diphenyl-2,2'-dicarboxylic acid, pyridine-2,6-dicarboxylic acid, thiophene-2,5-dicarboxylic acid, pyridine-3,4-dicarboxylic acid, pyridine-2,4-dicarboxylic acid, pyrazole-3,5-dicarboxylic acid, phthalic acid, terephthalic acid, thiophene-2,3-dicarboxylic acid, thiophene-3,4-dicarboxylic acid, thiophene-2,4-dicarboxylic acid, pyrazole-3,4-dicarboxylic acid, cyclohexane-1,2-dicarboxylic acid, cyclohexane-1,3-dicarboxylic acid, cyclohexane-1,4-dicarboxylic acid, cyclopentane-1,2-dicarboxylic acid, cyclopentane-1,3-dicarboxylic acid, cyclopentane-1,4-dicarboxylic acid, pyrrole-2,3-dicarboxylic acid, pyrrole-2,4-dicarboxylic acid, pyrrole-2,5-dicarboxylic acid, furan-2,3-dicarboxylic acid, furan-2,4-dicarboxylic acid or furan-2,5-dicarboxylic acid.

Preferably, the reaction time in step 1) is 3-4 h;

Preferably, in step 2), the mole ratio of gemcitabine hydrochloride, substituted acid obtained from step 1), benzotriazole-1-yl-oxytripyrrolidinylphosphonium hexafluorophosphate and 4-dimethylaminopyridine (DMP) is 1:(1.1-1.3):(1.1-1.3):(1.1-1.3).

The present invention also provides applications of the prodrugs based on the structure of gemcitabine, wherein the prodrugs are used in the manufacture of a drug for the treatment of lung cancer, pancreatic cancer, gastric cancer, breast cancer, colon cancer and liver cancer.

The beneficial effects of this invention are:

The organ specific prodrug research of the present invention is based on the study of the aforementioned prodrug of cytarabine with $O^5$ position cyclic phosphorylation. Gemcitabine which has better anti-cancer efficacy is used as the base structure of these nucleoside anti-cancer prodrugs. On the one hand, it can overcome the drug resistance of gemcitabine in lung cancer cells or pancreatic cancer cells. On the other hand, by modifying $N^4$ position with different substitutions, including aliphatic chains containing aromatic rings or different heterocyclic rings, the solubility, bioavailability and organ specificity of the drug are increased. The obtained prodrugs can overcome the defect of the fast-metabolism, reduce the toxicity of intestines caused by gemcitabine, improve its bioavailability, and make it usable by oral administration in clinics. Meanwhile, it can improve the drug's ability of anti-tumor, anti-cancer, anti-infection and anti-diffusion and can function in liver and colon specifically.

The synthetic route of the present invention use simple procedures, easily obtained materials with high yield, low cost and is suitable for industrial production.

The methods for preparing the prodrugs based on the structure of gemcitabine of the present invention, including the synthetic methods and screening methods, especially the researches regarding the methods and the components for treating various cancers and relevant diseases, can also apply to other nucleoside anti-cancer prodrugs containing cytosine, its substituents or 5-N-heterocytosine structures.

The present invention includes design, synthesis, pharmaceutical compositions and application methods of the related nucleoside prodrugs that may act directly on specific organ, as lung, liver or colon etc. i.e. organ specificities Furthermore, the present methods can be extended to other nucleoside anti-cancer drugs. So the present research is applicable to not only gemcitabine but also to and not limited to other nucleoside anti-cancer drugs, for example, azacytidine, decitabine, azacytosine, tiazofurine, nelarabine, 6-azauridine and cytarabine etc. The methods can also apply to the nucleoside anti-cancer drugs in clinical research, for instance, 2'-deoxy-2'-fluoro-methylc, 4'-thio-aracitidine, 4'-thiofluoro-aracitidin, 3'-ethynylcytidine etc. The nucleoside prodrugs with specific functions can be obtained through rational design and synthesis to overcome the toxicity of intestines caused by gemcitabine and improve its bioavailability and make it usable in oral administration in clinics and meanwhile to overcome the defect of activity losses due to the fast-metabolism of the nucleoside drugs in liver. The present research can develop a new treatment for late-stage liver and colon cancers.

EXAMPLES

The present invention is illustrated in more detail through the examples below. However, the present invention is not limited to the examples below in any way.

Gemcitabine hydrochloride was purchased from Ningbo Teampharm Co., Ltd.

(Benzotriazol-1-yl-oxy)tripyrrolidinylphosphonium hexafluorophosphate was purchased from GL Biochem (Shanghai) Ltd.

4-Dimethylaminopyridine was purchased from GL Biochem (Shanghai) Ltd.

Example 1

Dodecyl-2-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)benzoate (Compound No. 1)

The mixture of O-phthalic anhydride (5.0 g, 34 mmol), 1-dodecanol (7.5 g, 40 mmol) and 4-dimethylaminopyridine (240 mg, 2 mmol) were heated to melt and reacted for 4 hours, then cooled down to room temperature to produce a quantity of 2-(dodecyloxycarbonyl)benzoic acid.

Gemcitabine hydrochloride (0.7 g, 2.34 mmol), 2-(dodecyloxycarbonyl)benzoic acid (1.02 g, 3.04 mmol), (Benzotriazol-1-yl-oxy)tripyrrolidinylphosphonium hexafluorophosphate (1.34 g, 2.57 mmol), and 4-dimethylaminopyridine (428 mg, 3.51 mmol) were dissolved in N,N-dimethylformamide (10 mL) and stirred overnight at room temperature. The reaction mixture was poured into water, and then extracted three times with ethyl acetate. The isolated organic phase was dried with anhydrous $Na_2SO_4$. The solvent was removed by vaporizing under reduced pressure. The residue was purified by silica column chromatography (developing agent: dichloromethane/methanol=30/1) to produce 362.5 mg of Dodecyl-2-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)benzoate. LC purity 98% (UV254). LC-MS m/z 580 [M+H]$^+$ (molecular formula: $C_{29}H_{39}F_2N_3O_7$, molecule weight: 579). The structure and characterization data of the compound were shown in Table 1.

Example 2

Undecyl-2-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)benzoate (Compound No. 2)

The title compound was prepared according to the method described in Example 1 except for using 1-undecanol instead of 1-dodecanol. LC purity: 95% (UV 254). LC-MS m/z 566 [M+H]$^+$ (molecular formula: $C_{28}H_{37}F_2N_3O_7$, molecular weight: 565).

Example 3

Hexadecyl-2-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)benzoate (Compound No. 3)

The title compound was prepared according to the method described in Example 1 except for using 1-hexadecanol instead of 1-dodecanol, N,N-dimethylacetamide instead of N,N-dimethylformamide, and the reaction time of 6 h. LC purity 96% (UV 254). LC-MS m/z 636 [M+H]$^+$, (molecular formula: $C_{33}H_{47}F_2N_3O_7$, molecular weight: 635).

Example 4

Dodecyl-3-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)pyrazine-2-carboxylate (Compound No. 4, aftermentioned mark: SL-01)

Pyrazine-2,3-dicarboxylic acid (504 mg, 3.0 mmol) and DMF (2 drops) were added to 15 mL of $SOCl_2$. The reaction mixture was refluxed for 5 hours. The $SOCl_2$ was removed and 612 mg of pyrazine-2,3-dicarbonyl dichloride was nearly quantitatively obtained.

Pyrazine-2,3-dicarbonyl dichloride (612 mg, 3.0 mmol) was dissolved in dioxin (20 mL). 1-dodecanol (558 mg) and $Et_3N$ (2 mL) in dioxin (5 mL) was added dropwise into the solution under ice-water bath and reacted for 4 h and concentrated and dried to a solid state. The residue was dissolved in water where the pH value is adjusted to 2-3 and extracted three times with ethyl acetate. The isolated organic phase was dried with anhydrous $Na_2SO_4$. The solvent was removed by vaporizing under reduced pressure and 3-(dodecyloxycarbonyl)pyrazine-2-carboxylic acid was nearly quantitatively obtained.

Gemcitabine hydrochloride (500 mg, 1.67 mmol), 3-(dodecyloxycarbonyl)pyrazine-2-carboxylic acid (674 mg, 2.01 mmol), (Benzotriazol-1-yl-oxy)tripyrrolidinophosphonium hexafluorophosphate (955 mg, 1.84 mmol), and 4-dimethylaminopyridine (244 mg, 2.0 mmol) were dissolved in N,N-dimethylformamide (10 mL) and stirred at room temperature overnight. The reaction mixture was poured into water, then extracted three times with ethyl acetate. The isolated organic phase was dried with anhydrous $Na_2SO_4$. The solvent was removed by vaporizing under reduced pressure. The residue was purified by silica column chromatography (developing agent; dichloromethane/methanol=40/1) to produce 225.7 mg of dodecyl-3-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)pyrazine-2-carboxylate. LC purity 98% (UV 254). LC-MS m/z 582 [M+H]$^+$, (molecular formula: $C_{27}H_{37}F_2N_5O_7$, molecular weight: 581). The structure and characterization data of the compound were shown in Table 1.

Example 5

Undecyl-3-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)pyrazine-2-carboxylate (Compound No. 5)

The title compound was prepared according to the method described in Example 4 except for using 1-undecanol instead of 1-dodecanol, tetrahydrofuran instead of dioxin. LC purity 97% (UV 254). LC-MS m/z 568 [M+H]$^+$, (molecular formula: $C_{26}H_{35}F_2N_5O_7$, molecular weight: 567). The structure and characterization data of the compound were shown in Table 1.

Example 6

Decyl-3-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)benzoate (Compound No. 6)

The title compound was prepared according to the method described in Example 4 except for using m-phthalic acid instead of pyrazine-2,3-dicarboxylic acid, sulfolane instead of dioxin, 1-decanol instead of 1-dodecanol. LC purity 96% (UV 254 nm). LC-MS m/z 552 [M+H]$^+$, (molecular formula: $C_{27}H_{35}F_2N_3O_7$, molecular weight: 551).

Example 7

Undecyl-3-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)benzoate (Compound No. 7)

The title compound was prepared according to the method described in Example 4 except for using m-phthalic acid instead of pyrazine-2,3-dicarboxylic acid, dimethyl sulfoxide, 1-undecanol instead of 1-dodecanol instead of dioxin. LC purity 88% (UV 254 nm). LC-MS m/z 566 [M+H]$^+$, (molecular formula: $C_{28}H_{37}F_2N_3O_7$, molecular weight: 565).

Example 8

Dodecyl-6-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)nicotinate (Compound No. 8)

The title compound was prepared according to the method described in Example 4 except for using pyridine-2,5-dicarboxylic acid instead of pyrazine-2,3-dicarboxylic acid, and the reaction time of 3 h. LC purity 97% (dUV254 nm). LC-MS m/z 581 [M+H]$^+$, (molecular formula: $C_{28}H_{38}F_2N_4O_7$, molecular weight: 580). The structure and characterization data of the compound were shown in Table 1.

Example 9

Dodecyl-5-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)picolinate (Compound No. 9)

The title compound was prepared according to the method described in Example 4 except for using pyridine-2,5-dicarboxylic acid instead of pyrazine-2,3-dicarboxylic acid, pyridine instead of dioxin. LC purity 94% (UV 254 nm). LC-MS m/z 581 [M+H]$^+$, (molecular formula: $C_{28}H_{38}F_2N_4O_7$, molecular weight: 580). The structure and characterization data of the compound were shown in Table 1.

Example 10

Undecyl-6-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)nicotinate (Compound No. 10)

The title compound was prepared according to the method described in Example 4 except for using pyridine-2,5-dicarboxylic acid instead of pyrazine-2,3-dicarboxylic acid, 1-undecanol instead of 1-dodecanol. LC purity 99% (UV 254 nm). LC-MS m/z 567 [M+H]$^+$, (molecular formula: $C_{27}H_{36}F_2N_4O_7$, molecular weight: 566). The structure and data of the compound were shown in Table 1.

Example 11

Undecyl-5-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)picolinate (Compound No. 11)

The title compound was prepared according to the method described in Example 4 except for using pyridine-2,5-dicarboxylic acid instead of pyrazine-2,3-dicarboxylic acid, 1-undecanol instead of 1-dodecanol. LC purity 97% (UV 254 nm). LC-MS m/z 567 [M+H]$^+$, (molecular formula: $C_{27}H_{36}F_2N_4O_7$, molecular weight: 566). The structure and characterization data of the compound were shown in Table 1.

Example 12

Dodecyl-3-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)picolinate (Compound No. 12)

The title compound was prepared according to the method described in Example 4 except for using pyridine-2,3-dicarboxylic acid instead of pyrazine-2,3-dicarboxylic acid. LC purity 97% (UV 254 nm). LC-MS m/z 581 [M+H]$^+$, (molecular formula: $C_{28}H_{38}F_2N_4O_7$, molecular weight: 580).

Example 13

Dodecyl-2-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)nicotinate (Compound No. 13)

The title compound was prepared according to the method described in Example 4 except for using pyridine-2,3-dicarboxylic acid instead of pyrazine-2,3-dicarboxylic acid. LC purity 97% (UV 254 nm). LC-MS m/z 581 [M+H]$^+$, (molecular formula: $C_{28}H_{38}F_2N_4O_7$, molecular weight: 580).

Example 14

Undecyl-2-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)nicotinate (Compound No. 14)

The title compound was prepared according to the method described in Example 4 except for using pyridine-2,3-dicarboxylic acid instead of pyrazine-2,3-dicarboxylic acid, 1-undecanol instead of 1-dodecanol. LC purity 98% (UV 254 nm). LC-MS m/z 567 [M+H]$^+$, (molecular formula: $C_{27}H_{36}F_2N_4O_7$, molecular weight: 566).

Example 15

Undecyl-3-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)picolinate (Compound No. 15)

The title compound was prepared according to the method described in Example 4 except for using pyridine-2,3-dicarboxylic acid instead of pyrazine-2,3-dicarboxylic acid, 1-undecanol instead of 1-dodecanol. LC purity 97% (UV 254 nm). LC-MS m/z 567 [M+H]$^+$, (molecular formula: $C_{27}H_{36}F_2N_4O_7$, molecular weight: 566). The structure and characterization data of the compound were shown in Table 1.

Example 16

Methyl-2-(2-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)phenyl-1-yl)benzoate (Compound No. 16)

The title compound was prepared according to the method described in Example 4 except for using biphenyl-2,2'-dicarboxylic acid instead of pyrazine-2,3-dicarboxylic acid, methanol instead of 1-dodecanol. LC purity 86% (UV 254 nm). LC-MS m/z 502 [M+H]$^+$, (molecular formula: $C_{24}H_{21}F_2N_3O_7$, molecular weight: 501).

Example 17

Dodecyl-2-(2-((1-((2R,4R,5R)-3,3-difluoro-4-hydroxy-5-(hydroxymethyl)-tetrahydrofuran-yl)-2-oxo-1,2-dihydropyrimidin-4-yl)carbamoyl)phenyl-1-yl)benzoate (Compound No. 17)

The title compound was prepared according to the method described in Example 4 except for using biphenyl-2,2'-dicarboxylic acid instead of pyrazine-2,3-dicarboxylic acid. LC purity 98% (UV 254 nm). LC-MS m/z 656 [M+H]$^+$, (molecular formula: $C_{35}H_{43}F_2N_3O_7$, molecular weight: 655).

Example 18

Dodecyl-6-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)picolinate (Compound No. 18)

The title compound was prepared according to the method described in Example 4 except for using pyridine-2,6-dicarboxylic acid instead of pyrazine-2,3-dicarboxylic acid. LC purity 96% (UV 254 nm). LC-MS m/z 581 [M+H]$^+$, (molecular formula: $C_{28}H_{38}F_2N_4O_7$, molecular weight: 580).

Example 19

Undecyl-6-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)picolinate (Compound No. 19)

The title compound was prepared according to the method described in Example 4 except for using pyridine-2,6-dicarboxylic acid instead of pyrazine-2,3-dicarboxylic acid, n-undecanol instead of 1-dodecanol. LC purity 95% (UV 254 nm). LC-MS m/z 567 [M+H]$^+$, (molecular formula: $C_{27}H_{36}F_2N_4O_7$, molecular weight: 566).

Example 20

Dodecyl-5-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)thiophene-2-carboxylate (Compound No. 20)

The title compound was prepared according to the method described in Example 4 except for using thiophene-2,5-dicarboxylic acid instead of pyrazine-2,3-dicarboxylic acid. LC purity 95% (UV 254 nm). LC-MS m/z 586 [M+H]$^+$, (molecular formula: $C_{27}H_{37}F_2N_3O_7S$, molecular weight: 585). The structure and characterization data of the compound were shown in Table 1.

Example 21

Undecyl-5-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)thiophene-2-carboxylate (Compound No. 21)

The title compound was prepared according to the method described in Example 4 except for using thiophene-2,5-dicarboxylic acid instead of pyrazine-2,3-dicarboxylic acid, 1-undecanol instead of 1-dodecanol. LC purity 90% (UV 254 nm). LC-MS m/z 572 [M+H]$^+$, (molecular formula: $C_{26}H_{35}F_2N_3O_7S$, molecular weight: 571).

Example 22

Undecyl-3-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)isonicotinate (Compound No. 22)

The title compound was prepared according to the method described in Example 4 except for using pyridine-3,4-dicarboxylic acid instead of pyrazine-2,3-dicarboxylic acid, 1-undecanol instead of 1-dodecanol. LC purity 97% (UV 254 nm). LC-MS m/z 567 [M+H]$^+$, (molecular formula: $C_{27}H_{36}F_2N_4O_7$, molecular weight: 566). The structure and characterization data of the compound were shown in Table 1.

Example 23

Undecyl-4-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)nicotinate (Compound No. 23)

The title compound was prepared according to the method described in Example 4 except for using pyridine-3,4-dicarboxylic acid instead of pyrazine-2,3-dicarboxylic acid, 1-undecanol instead of 1-dodecanol. LC purity 97% (UV 254 nm). LC-MS m/z 567 [M+H]$^+$, (molecular formula: $C_{27}H_{36}F_2N_4O_7$, molecular weight: 566). The structure and characterization data of the compound were shown in Table 1.

Example 24

Dodecyl-3-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)isonicotinate (Compound No. 24)

The title compound was prepared according to the method described in Example 4 except for using pyridine-3,4-dicarboxylic acid instead of pyrazine-2,3-dicarboxylic acid. LC purity 95% (UV 254 nm). LC-MS m/z 581 [M+H]$^+$, (molecular formula: $C_{28}H_{38}F_2N_4O_7$, molecular weight: 580).

Example 25

Dodecyl-4-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)nicotinate (Compound No. 25)

The title compound was prepared according to the method described in Example 4 except for using pyridine-3,4-dicarboxylic acid instead of pyrazine-2,3-dicarboxylic acid. LC purity 95% (UV 254 nm). LC-MS m/z 581 [M+H]$^+$, (molecular formula: $C_{28}H_{38}F_2N_4O_7$, molecular weight: 580).

Example 26

Dodecyl-2-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)isonicotinate (Compound No. 26)

The title compound was prepared according to the method described in Example 4 except for using pyridine-2,4-dicarboxylic acid instead of pyrazine-2,3-dicarboxylic acid. LC purity 96% (UV 254 nm). LC-MS m/z 581 [M+H]$^+$, (molecular formula: $C_{28}H_{38}F_2N_4O_7$, molecular weight: 580). The structure and characterization data of the compound were shown in Table 1.

Example 27

Dodecyl-4-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)picolinate (Compound No. 27)

The title compound was prepared according to the method described in Example 4 except for using pyridine-2,4-dicarboxylic acid instead of pyrazine-2,3-dicarboxylic acid. LC purity 86% (UV 254 nm). LC-MS m/z 581 [M+H]$^+$, (molecular formula: $C_{28}H_{38}F_2N_4O_7$, molecular weight: 580).

Example 28

Undecyl-2-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)isonicotinate (Compound No. 28)

The title compound was prepared according to the method described in Example 4 except for using pyridine-2,4-dicarboxylic acid instead of pyrazine-2,3-dicarboxylic acid, 1-undecanol instead of 1-dodecanol. LC purity 90% (UV 254 nm). LC-MS m/z 567 [M+H]$^+$, (molecular formula: $C_{27}H_{36}F_2N_4O_7$, molecular weight: 566). The structure and characterization data of the compound were shown in Table 1.

Example 29

Undecyl-4-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)picolinate (Compound No. 29)

The title compound was prepared according to the method described in Example 4 except for using pyridine-2,4-dicarboxylic acid instead of pyrazine-2,3-dicarboxylic acid, 1-undecanol instead of 1-dodecanol. LC purity 90% (UV 254 nm). LC-MS m/z 567 [M+H]$^+$, (molecular formula: $C_{27}H_{36}F_2N_4O_7$, molecular weight: 566).

Example 30

Undecyl-5-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)-1H-pyrazole-3-carboxylate (Compound No. 30)

The title compound was prepared according to the method described in Example 4 except for using pyrazole-3,5-dicarboxylic acid instead of pyrazine-2,3-dicarboxylic acid, 1-undecanol instead of 1-dodecanol. LC purity 99% (UV 254 nm). LC-MS m/z 556 [M+H]$^+$, (molecular formula: $C_{25}H_{35}F_2N_5O_7$, molecular weight: 555). The structure and characterization data of the compound were shown in Table 1.

Example 31

Dodecyl-5-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)-1H-pyrazole-3-carboxylate (Compound No. 31)

The title compound was prepared according to the method described in Example 4 except for using pyrazole-3,5-dicarboxylic acid instead of pyrazine-2,3-dicarboxylic acid. LC purity 98% (UV 254 nm). LC-MS m/z 570 [M+H]$^+$, (molecular formula: $C_{26}H_{37}F_2N_5O_7$, molecular weight: 569).

Example 32

Undecyl-2-(2-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)phenyl)acetate (Compound No. 32)

The title compound was prepared according to the method described in Example 1 except for using homophthalic anhydride instead of o-phthalic anhydride, 1-undecanol instead of 1-dodecanol. LC purity 96% (UV 254 nm). LC-MS m/z 636 [M+H]$^+$, (molecular formula: $C_{33}H_{47}F_2N_3O_7$, molecular weight: 635).

Example 33

Undecyl-2-(2-(1-((2R,4R,5R)-3,3-difluoro-4-hydroxy-5-(hydroxymethyl)-tetrahydrofuran-2-yl)-2-oxo-1,2-dihydropyrimidin-4-ylamino)-2-oxoethyl)benzoate (Compound No. 33)

The title compound was prepared according to the method described in Example 1 except for using homophthalic anhydride instead of o-phthalic anhydride, 1-undecanol instead of 1-dodecanol. LC purity 90% (UV 254 nm). LC-MS m/z 580 [M+H]$^+$, (molecular formula: $C_{29}H_{39}F_2N_3O_7$, molecular weight: 579).

Example 34

Dodecyl-2-(2-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)phenyl)acetate (Compound No. 34)

The title compound was prepared according to the method described in Example 1 except for using homophthalic acid instead of o-phthalic anhydride. LC purity 93% (UV 254 nm). LC-MS m/z 594 [M+H]$^+$, (molecular formula: $C_{30}H_{41}F_2N_3O_7$, molecular weight: 593).

Example 35

Dodecyl-2-(2-(1-((2R,4R,5R)-3,3-difluoro-4-hydroxy-5-(hydroxymethyl)-tetrahydrofuran-2-yl)-2-oxo-1,2-dihydropyrimidin-4-ylamino)-2-oxoethyl)benzoate (Compound No. 35)

The title compound was prepared according to the method described in Example 1 except for using homophthalic anhydride instead of o-phthalic anhydride. LC purity 93% (UV 254 nm). LC-MS m/z 594 [M+H]$^+$, (molecular formula: $C_{30}H_{41}F_2N_3O_7$, molecular weight: 593).

Example 36

Undecyl-2-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)cyclohexanecarboxylate (Compound No. 36)

The title compound was prepared according to the method described in Example 1 except for using cyclohexane-1,2-dicarboxylic anhydride instead of o-phthalic anhydride, 1-undecanol instead of 1-dodecanol. LC purity 95% (UV 254 nm). LC-MS m/z 572 [M+H]$^+$, (molecular formula: a $C_{28}H_{43}F_2N_3O_7$, molecular weight: 571).

Example 37

$N^2$-(1-((2R,4R,5R)-3,3-difluoro-4-hydroxy-5-(hydroxymethyl)-tetrahydrofuran-2-yl)-2-oxo-1,2-dihydropyrimidin-4-yl)-$N^3$-dodecylpyrazine-2,3-dicarboxamide (Compound No. 37)

Pyrazine-2,3-dicarboxylic acid (624 mg, 4.0 mmol), 1-dodecylamine (740 mg, 4.0 mmol), benzotriazole-1-yl-oxytripyrrolidinylphosphonium hexafluorophosphate (2.6 g, 4.8 mmol) and 4-dimethylaminopyridine (488 mg, 0.4 mmol) were dissolved in N,N-dimethylformamide (10 mL) and stirred at room temperature overnight. The reaction mixture was poured into water, then extracted three times with ethyl acetate. The isolated organic phase was dried with anhydrous $Na_2SO_4$. The solvent was removed by vaporizing under reduced pressure. The residue was purified by silica column chromatography (developing agent: dichloromethane/methanol=30/1) to produce 3-(dodecylcarbamoyl)pyrazine-2-carboxylic acid (650 mg).

Gemcitabine hydrochloride (200 mg, 0.67 mmol), 3-(dodecylcarbamoyl)pyrazine-2-carboxylic acid (325 mg, 1.01 mmol), benzotriazole-1-yl-oxytripyrrolidinylphosphonium hexafluorophosphate (327.6 mg, 0.74 mmol), and 4-dimethylaminopyridine (98 mg, 0.80 mmol) were dissolved in N,N-Dimethylformamide (10 mL) and stirred at room temperature overnight. The reaction mixture was poured into the water, then extracted three times with ethyl acetate. The isolated organic phase was dried with anhydrous $Na_2SO_4$. The solvent was removed by vaporizing under reduced pressure. The residue was purified by silica column chromatography (developing agent: dichloromethane/methanol=10/1) to produce 290 mg of N2-(1-((2R,4R,5R)-3,3-difluoro-4-hydroxy-5-(hydroxymethyl)-tetrahydrofuran-2-yl)-2-oxo-1,2-dihydropyrimidin-4-yl)-N-3-dodecylpyrazine-2,3-dicarboxamide (compound No. 37). LC purity 98% (UV 254). LC-MS m/z 581 [M+H]$^+$, (molecular formula: $C_{27}H_{38}F_2N_6O_6$, molecular weight: 580). The structure and characterization data of the compound were shown in Table 1.

Example 38

Dodecyl-6-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)pyridazine-3-carboxylate (Compound No. 38)

The title compound was prepared according to the method described in Example 4 except using pyridazine-3,6-carboxylic acid instead of pyrazine-2,3-dicarboxylic acid. LC purity 95% (UV 254 nm). LC-MS m/z 582 [M+H]$^+$, (molecular formula: $C_{27}H_{37}F_2N_5O_7$, MW: 581).

Example 39

Dodecyl-6-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)pyrimidine-4-carboxylate (Compound No. 39)

The title compound was prepared according to the method described in Example 4 except using pyrimidine-4,5-dicarboxylic acid instead of pyrazine-2,3-dicarboxylic acid. LC purity 96% (UV 254 nm). LC-MS m/z 582 [M+H]$^+$, (molecular formula: $C_{27}H_{37}F_2N_5O_7$, MW: 581).

TABLE 1

| | Structure and Characterization Data of the Compounds | | |
|---|---|---|---|
| No. | Name | Structure | Data |
| NO. 1 | Dodecyl 2-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)benzoate | | LC (UV254) purity 98%. LC-MS m/z 580 [M + H]$^+$ $^1$HNMR (DMSO, 600 MHz) δ = 0.85 (t, 3H), 1.17-1.25 (m, 18H), 1.55 (m, 2H), 3.67 (m, 1H), 3.82 (m, 1H), 3.91 (m, 1H), 4.18 (t, 2H), 4.23 (m, 1H), 5.33 (t, 1H), 6.18 (t, 1H), 6.34 (d, 1H), 7.39 (d, 1H), 7.58 (d, 1H), 7.62 (t, 1H), 7.68 (t, 1H), 7.88 (d, 1H), 8.33 (d, 1H), 11.56 (S, 1H). |
| NO. 2 | Undecyl 2-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)benzoate | | LC (UV254) purity 95%. LC-MS m/z 566 [M + H]$^+$ |

TABLE 1-continued

Structure and Characterization Data of the Compounds

| No. | Name | Structure | Data |
| --- | --- | --- | --- |
| NO. 3 | Hexadecyl 2-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)benzoate | 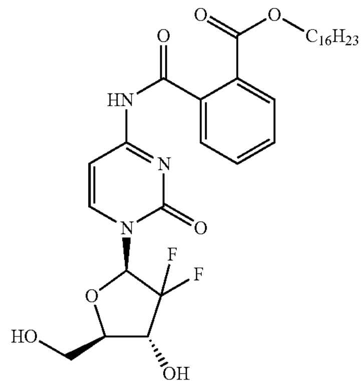 | LC (UV254) purity 96%. LC-MS m/z 636 [M + H]$^+$ |
| NO. 4 | Dodecyl 3-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)pyrazine-2-carboxylate | 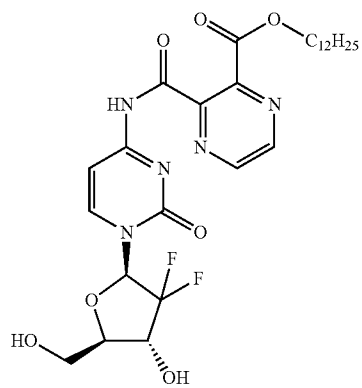 | LC (UV254) purity 98%. LC-MS m/z 582 [M + H]$^+$ $^1$HNMR (DMSO, 600 MHz) δ = 0.85 (t, 3H), 1.22-1.30 (m, 18H), 1.62 (m, 2H), 3.67 (m, 1H), 3.82 (m, 1H), 3.92 (m, 1H), 4.21 (m, 1H), 4.30 (t, 2H), 5.33 (t, 1H), 6.18 (t, 1H), 6.34 (d, 1H), 7.28 (d, 1H), 8.38 (d, 1H), 8.94 (dd, 2H), 11.50 (S, 1H). |
| NO. 5 | Undecyl 3-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)pyrazine-2-carboxylate | 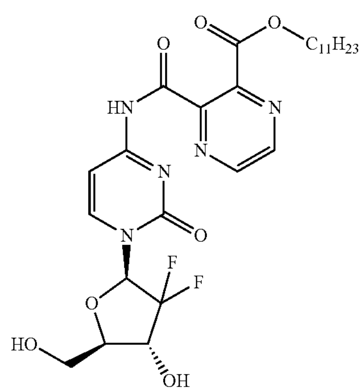 | LC (UV254) purity 97%. LC-MS m/z 568 [M + H]$^+$ $^1$HNMR (DMSO, 600 MHz) δ = 0.85 (t, 3H), 1.22-1.30 (m, 16H), 1.62 (m, 2H), 3.67 (m, 1H), 3.82 (m, 1H), 3.92 (m, 1H), 4.21 (m, 1H), 4.29 (t, 2H), 5.35 (t, 1H), 6.18 (t, 1H), 6.35 (d, 1H), 7.28 (d, 1H), 8.38 (d, 1H), 8.94 (dd, 2H), 11.51 (S, 1H). |
| NO. 6 | Decyl 3-((1-((2R,4R,5R)-3,3-difluoro-4-hydroxy-5-(hydroxymethyl)-tetrahydofuran-2-yl)-2-oxo-1,2-dihydropyrimidin-4-yl)carbamoyl)benzoate | 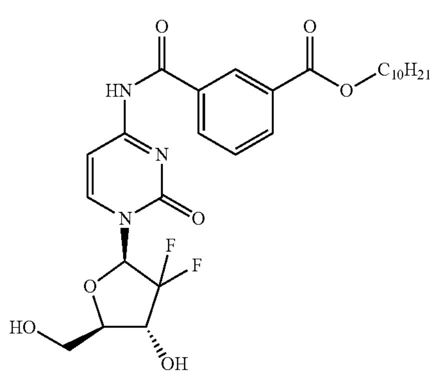 | LC (UV254) purity 96%. LC-MS m/z 636 [M + H]$^+$ |

TABLE 1-continued

Structure and Characterization Data of the Compounds

| No. | Name | Structure | Data |
|---|---|---|---|
| NO. 7 | Undecyl 3-((1-((2R,4R,5R)-3,3-difluoro-4-hydroxy-5-(hydroxymethyl)-tetrahydofuran-2-yl)-2-oxo-1,2-dihydropyrimidin-4-yl)carbamoyl)benzoate | 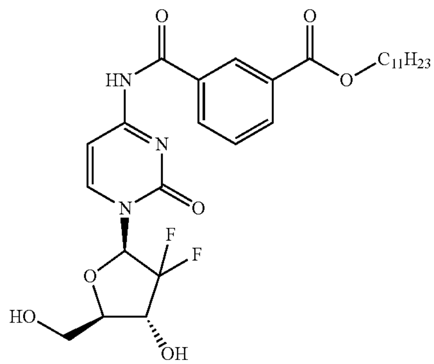 | LC (UV254) purity 88%. LC-MS m/z 566 [M + H]$^+$ |
| NO. 8 | Dodecyl 6-((1-((2R,4R,5R)-3,3-difluoro-4-hydroxy-5-(hydroxymethyl)-tetrahydrofuran-2-yl)-2-oxo-1,3-dihydropyrimidin-4-yl)carbamoyl)nicotinate | 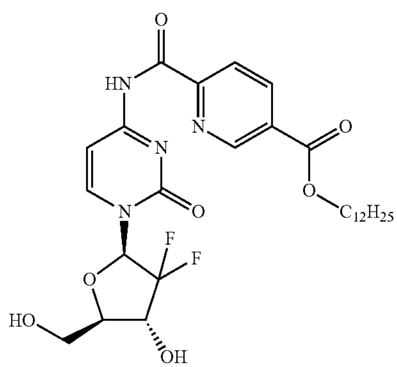 | LC (UV254) purity 97%. LC-MS m/z 581 [M + H]$^+$ $^1$HNMR (DMSO, 600 MHz) δ = 0.84 (t, 3H), 1.23-1.30 (m, 18H), 1.72 (m, 2H), 3.67 (m, 1H), 3.82 (m, 1H), 3.92 (m, 1H), 4.22 (m, 1H), 4.35 (t, 2H), 5.37 (t, 1H), 6.21 (t, 1H), 6.37 (d, 1H), 7.45 (d, 1H), 6.37 (d, 1H), 7.45 (d, 1H), 8.32 (d, 1H), 8.44 (d, 1H), 8.57 (d, 1H), 9.21 (S, 1H), 10.65 (S, 1H). |
| NO. 9 | Dodecyl 5-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)picolinate | 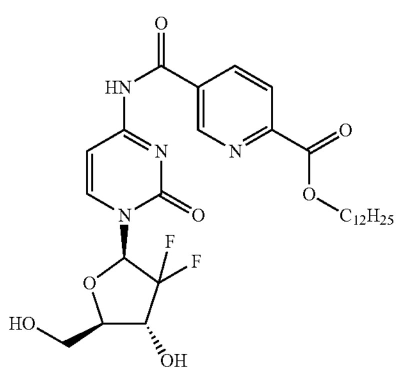 | LC (UV254) purity 94%. LC-MS m/z 581 [M + H]$^+$ $^1$HNMR (DMSO, 600 MHz) δ = 0.84 (t, 3H), 1.23-1.33 (m, 18H), 1.72 (m, 2H), 3.67 (m, 1H), 3.83 (m, 1H), 3.93 (m, 1H), 4.22 (m, 1H), 4.33 (t, 2H), 5.35 (t, 1H), 6.22 (t, 1H), 6.35 (d, 1H), 7.39 (d, 1H), 8.15 (d, 1H), 8.36 (d, 1H), 8.50 (d, 1H), 9.20 (S, 1H), 11.82 (S, 1H). |
| NO. 10 | Undecyl 6-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)nicotinate | 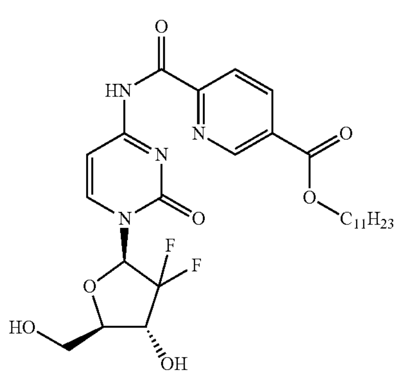 | LC (UV254) purity 99%. LC-MS m/z 567 [M + H]$^+$ $^1$HNMR (DMSO, 600 MHz) δ = 0.84 (t, 3H), 1.24-1.44 (m, 16H), 1.73 (m, 2H), 3.68 (m, 1H), 3.82 (m, 1H), 3.93 (m, 1H), 4.22 (m, 1H), 4.35 (t, 2H), 5.38 (t, 1H), 6.21 (t, 1H), 6.38 (d, 1H), 7.45 (d, 1H), 8.32 (d, 1H), 8.44 (d, 1H), 8.57 (d, 1H), 9.20 (S, 1H), 10.64 (S, 1H). |

TABLE 1-continued

Structure and Characterization Data of the Compounds

| No. | Name | Structure | Data |
|---|---|---|---|
| NO. 11 | Undecyl 5-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)picolinate | 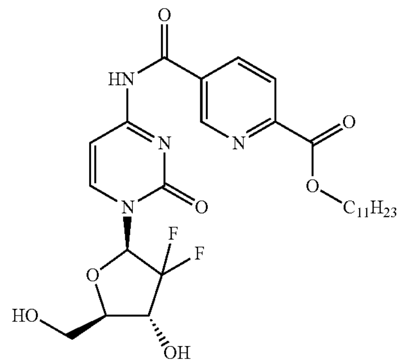 | LC (UV254) purity 97%. LC-MS m/z 567 [M + H]$^+$ $^1$HNMR (DMSO, 600 MHz) δ = 0.85 (t, 3H), 1.23-1.39 (m, 18H), 1.73 (m, 2H), 3.68 (m, 1H), 3.83 (m, 1H), 3.93 (m, 1H), 4.22 (m, 1H), 4.33 (t, 2H), 5.35 (t, 1H), 6.22 (t, 1H), 6.35 (d, 1H), 7.39 (d, 1H), 8.15 (d, 1H), 8.36 (d, 1H), 8.50 (d, 1H), 9.20 (S, 1H), 11.81 (S, 1H). |
| NO. 12 | Dodecyl 3-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)picolinate | 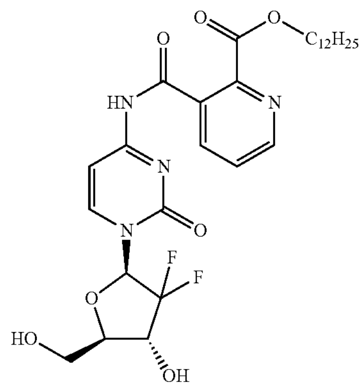 | LC (UV254) purity 97%. LC-MS m/z 581 [M + H]$^+$ $^1$HNMR (DMSO, 600 MHz) δ = 0.85 (t, 3H), 1.18-1.27 (m, 18H), 1.58 (m, 2H), 3.67 (m, 1H), 3.82 (m, 1H), 3.91 (m, 1H), 4.25 (m, 3H), 5.33 (t, 1H), 6.19 (t, 1H), 6.34 (d, 1H), 7.35 (d, 1H), 7.70 (dd, 1H), 8.13 (d, 1H), 8.35 (d, 1H), 8.76 (d, 1H), 11.72 (s, 1H). |
| NO. 13 | Dodecyl 2-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)nicotinate | 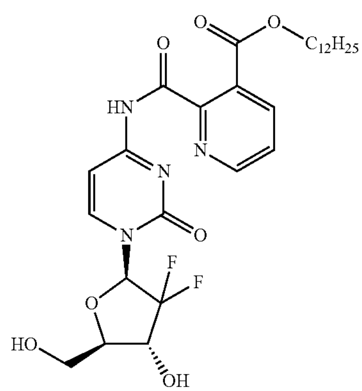 | LC (UV254) purity 97%. LC-MS m/z 581 [M + H]$^+$ |
| NO. 14 | Undecyl 2-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)nicotinamide | 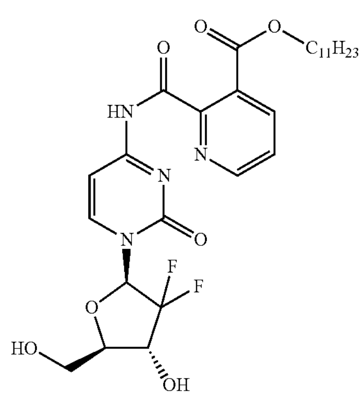 | LC (UV254) purity 98%. LC-MS m/z 567 [M + H]$^+$ |

TABLE 1-continued

Structure and Characterization Data of the Compounds

| No. | Name | Structure | Data |
|---|---|---|---|
| NO. 15 | Undecyl 3-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)picolinate | 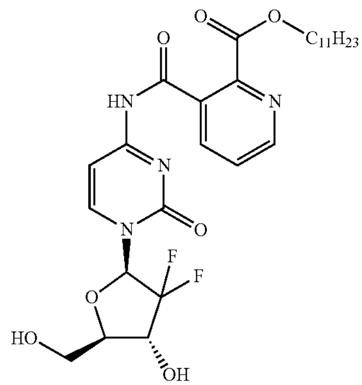 | LC (UV254) purity 97%. LC-MS m/z 567 [M + H]$^+$ $^1$HNMR (DMSO, 600 MHz) δ = 0.85 (t, 3H), 1.18-1.27 (m, 16H), 1.58 (m, 2H), 3.67 (m, 1H), 3.82 (m, 1H), 3.91 (m, 1H), 4.21 (m, 3H), 5.33 (t, 1H), 6.19 (t, 1H), 6.34 (d, 1H), 7.35 (d, 1H), 7.70 (dd, 1H), 8.13 (d, 1H), 8.35 (d, 1H), 8.77 (d, 1H), 11.72 (s, 1H). |
| NO. 16 | Methyl 2-(2-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)phenyl-1-yl)benzoate | 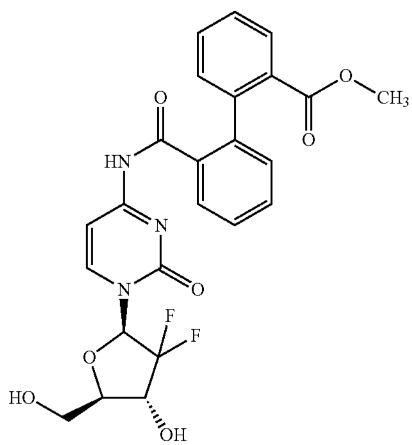 [SMILES: COC(=O)c1ccccc1-c1ccccc1C(=O)Nc1ccn([C@@H]2O[C@H](CO)[C@@H](O)C2(F)F)c(=O)n1] | LC (UV254) purity 86%. LC-MS m/z 502 [M + H]$^+$ |
| NO. 17 | Dodecyl 2-(2-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)phenyl-1-yl)benzoate | 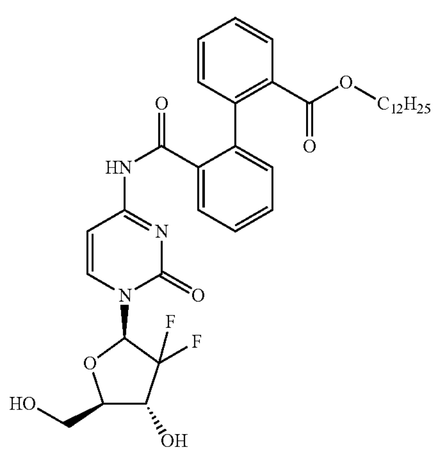 | LC (UV254) purity 98%. LC-MS m/z 656 [M + H]$^+$ |

TABLE 1-continued

Structure and Characterization Data of the Compounds

| No. | Name | Structure | Data |
|---|---|---|---|
| NO. 18 | Dodecyl 6-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)picolinate | 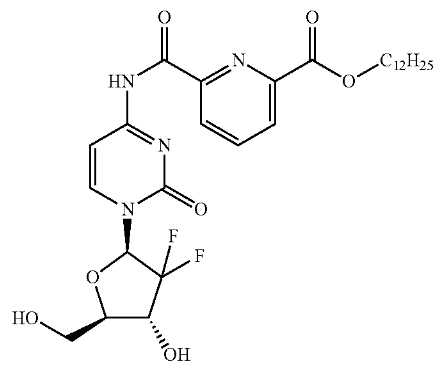 | LC (UV254) purity 96%. LC-MS m/z 581 [M + H]$^+$ $^1$HNMR (DMSO, 600 MHz) δ = 0.84 (t, 3H), 1.23-1.28 (m, 18H), 1.73 (m, 2H), 3.68 (m, 1H), 3.82 (m, 1H), 3.92 (m, 1H), 4.24 (m, 1H), 4.40 (t, 2H), 5.37 (t, 1H), 6.23 (t, 1H), 6.37 (d, 1H), 7.48 (d, 1H), 8.33 (t, 1H), 8.36 (dd, 1H), 8.41 (dd, 1H), 8.44 (d, 1H), 10.47 (s, 1H). |
| NO. 19 | Undecyl 6-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)picolinate | 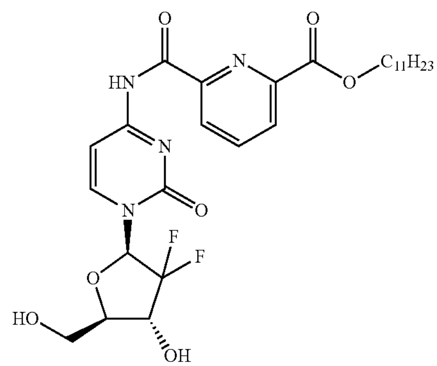 | LC (UV254) purity 95%. LC-MS m/z 567 [M + H]$^+$ |
| NO. 20 | Dodecyl 5-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)thiophene-2-carboxylate | 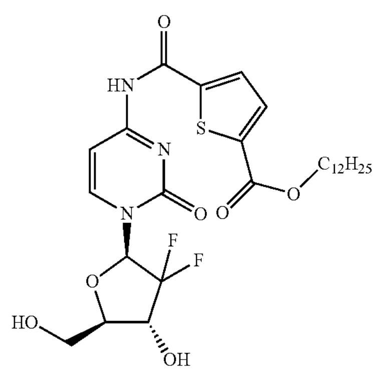 | LC (UV254) purity 95%. LC-MS m/z 586 [M + H]$^+$ $^1$HNMR (DMSO, 600 MHz) δ = 0.84 (t, 3H), 1.18-1.29 (m, 18H), 1.68 (m, 2H), 3.67 (m, 1H), 3.81 (m, 1H), 3.92 (m 1H), 4.20 (m, 1H), 4.28 (t, 2H), 5.35 (t, 1H), 6.20 (t, 1H), 6.35 (d, 1H), 7.36 (brs, 1H), 7.83 (d, 1H), 8.32 (brd, 2H), 11.75 (S, 1H). |
| NO. 21 | Undecyl 5-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)thiophene-2-carboxylate | 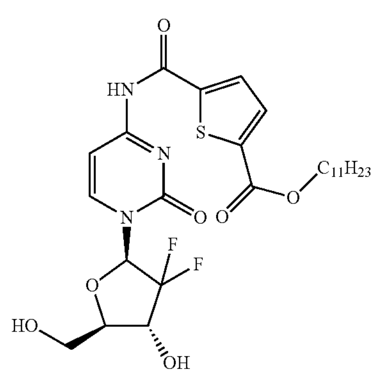 | LC (UV254) purity 90%. LC-MS m/z 572 [M + H]$^+$ |

TABLE 1-continued

Structure and Characterization Data of the Compounds

| No. | Name | Structure | Data |
|---|---|---|---|
| NO. 22 | Undecyl 3-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)isonicotinate | 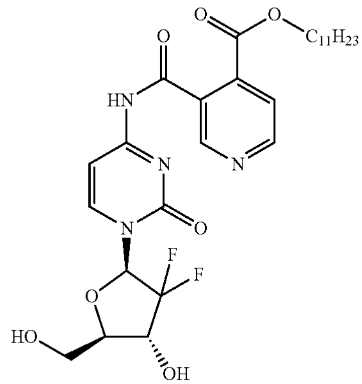 | LC (UV254) purity 97%. LC-MS m/z 567 [M + H]$^+$ $^1$HNMR (DMSO, 600 MHz) δ = 0.85 (t, 3H), 1.17-1.26 (m, 16H), 1.56 (m, 2H), 3.67 (m, 1H), 3.82 (m, 1H), 3.92 (m, 1H), 4.24 (m, 3H), 5.33 (t, 1H), 6.19 (t, 1H), 6.35 (d, 1H), 7.37 (d, 1H), 7.63 (d, 1H), 8.36 (d, 1H), 8.87 (d, 1H), 8.89 (d, 1H), 11.71 (S, 1H). |
| NO. 23 | Undecyl 4-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)nicotinate | 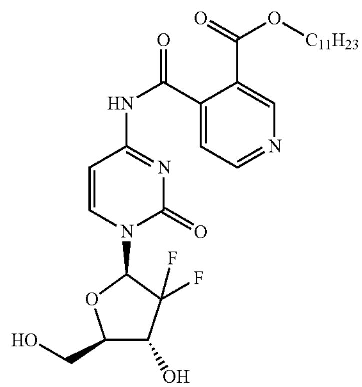 | LC (UV254) purity 97%. LC-MS m/z 567 [M + H]$^+$ $^1$HNMR (DMSO, 600 MHz) δ = 0.85 (t, 3H), 1.17-1.26 (m, 16H), 1.56 (m, 2H), 3.67 (m, 1H), 3.82 (m, 1H), 3.92 (m, 1H), 4.24 (m, 3H), 5.33 (t, 1H), 6.19 (t, 1H), 6.35 (d, 1H), 7.37 (d, 1H), 7.79 (d, 1H), 8.36 (d, 1H), 8.87 (d, 1H), 9.08 (s, 1H), 11.77 (S, 1H). |
| NO. 24 | Dodecyl 3-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)isonicotinate | 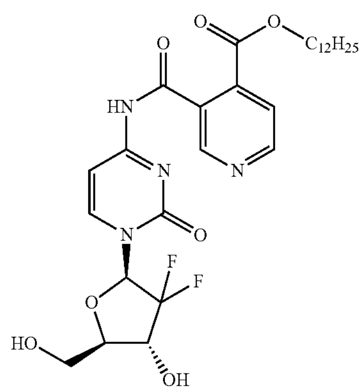 | LC (UV254) purity 95%. LC-MS m/z 581 [M + H]$^+$ |
| NO. 25 | Dodecyl 4-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)nicotinate | 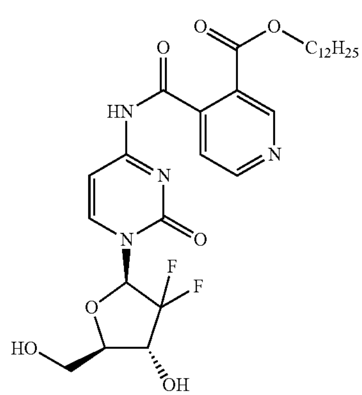 | LC (UV254) purity 95%. LC-MS m/z 581 [M + H]$^+$ |

TABLE 1-continued

Structure and Characterization Data of the Compounds

| No. | Name | Structure | Data |
|---|---|---|---|
| NO. 26 | Dodecyl 2-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)isonicotinate | 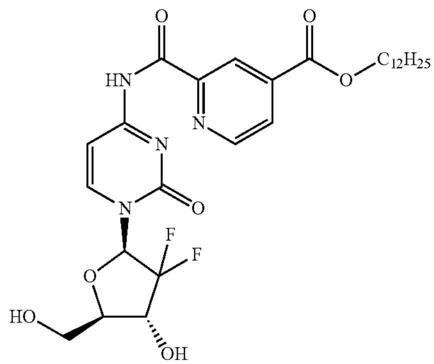 | LC (UV254) purity 96%. LC-MS m/z 581 [M + H]$^+$ $^1$HNMR (DMSO, 600 MHz) δ = 0.84 (t, 3H), 1.22-1.43 (m, 18H), 1.73 (m, 2H), 3.67 (m, 1H), 3.83 (m, 1H), 3.93 (m, 1H), 4.22 (m, 1H), 4.36 (t, 2H), 5.36 (t, 1H), 6.21 (t, 1H), 6.36 (d, 1H), 7.47 (d, 1H), 8.17 (d, 1H), 8.43 (d, 1H), 8.49 (s, 1H), 8.98 (d, 1H), 10.62 (S, 1H). |
| NO. 27 | Dodecyl 4-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)picolinate | 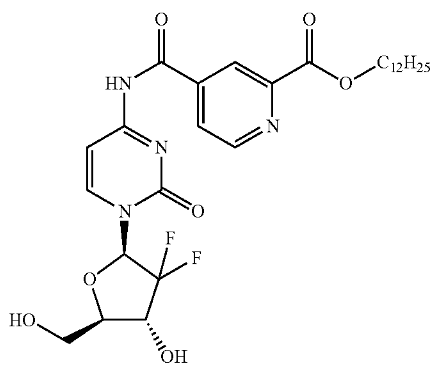 | LC (UV254) purity 86%. LC-MS m/z 581 [M + H]$^+$ $^1$HNMR (DMSO, 600 MHz) δ = 0.85 (t, 3H), 1.23-1.39 (m, 18H), 1.73 (m, 2H), 3.67 (m, 1H), 3.83 (m, 1H), 3.93 (m, 1H), 4.22 (m, 1H), 4.35 (t, 2H), 5.37 (t, 1H), 6.22 (t, 1H), 6.36 (d, 1H), 7.38 (d, 1H), 8.05 (d, 1H), 8.37 (d, 1H), 8.49 (s, 1H), 8.95 (d, 1H), 11.88 (S, 1H). |
| NO. 28 | Undecyl 2-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)isonicotinate | 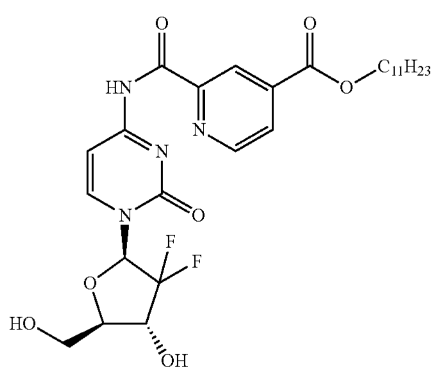 | LC (UV254) purity 90%. LC-MS m/z 567 [M + H]$^+$ $^1$HNMR (DMSO, 600 MHz) δ = 0.84 (t, 3H), 1.22-1.43 (m, 16H), 1.73 (m, 2H), 3.67 (m, 1H), 3.83 (m, 1H), 3.93 (m, 1H), 4.22 (m, 1H), 4.36 (t, 2H), 5.37 (t, 1H), 6.21 (t, 1H), 6.36 (d, 1H), 7.47 (d, 1H), 8.17 (d, 1H), 8.43 (d, 1H), 8.49 (s, 1H), 8.98 (d, 1H), 10.62 (S, 1H). |
| NO. 29 | Undecyl 4-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)picolinate | 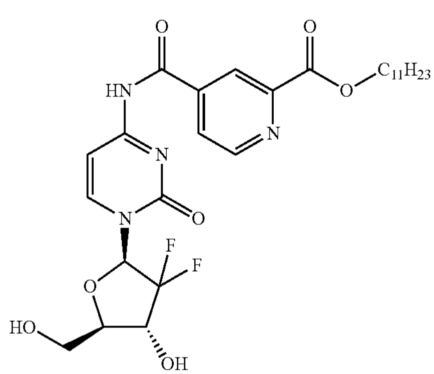 | LC (UV254) purity 90%. LC-MS m/z 567 [M + H]$^+$ |

TABLE 1-continued

Structure and Characterization Data of the Compounds

| No. | Name | Structure | Data |
|---|---|---|---|
| NO. 30 | Undecyl 5-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)-1H-pyrazole-3-carboxylate | 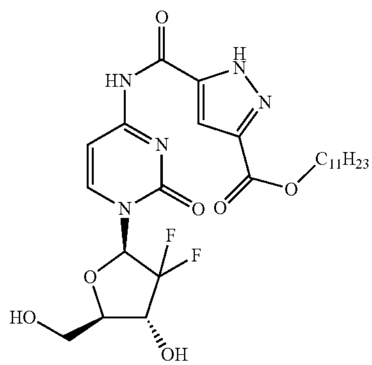 | LC (UV254) purity 99%. LC-MS m/z 556 [M + H]+ $^1$HNMR (DMSO, 600 MHz) δ = 0.84 (t, 3H), 1.16-1.40 (m, 16H), 1.68 (m, 2H), 3.67 (m, 1H), 3.82 (m, 1H), 3.91 (m, 1H), 4.22 (m, 1H), 4.26 (t, 2H), 5.36 (t, 1H), 6.20 (t, 1H), 6.35 (d, 1H), 7.41 (d, 1H), 7.50-7.91 (brd, 1H), 8.35 (d, 1H), 10.56-11.61 (brd, 1H), 14.60-14.80 (brd, 1H). |
| NO. 31 | Dodecyl 5-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)-1H-pyrazole-3-carboxylate | 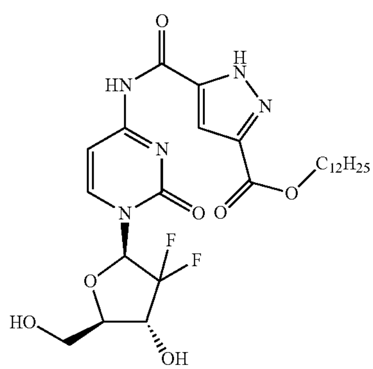 | LC (UV254) purity 98%. LC-MS m/z 570 [M + H]+ |
| NO. 32 | Undecyl 2-(2-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)phenyl)acetate | 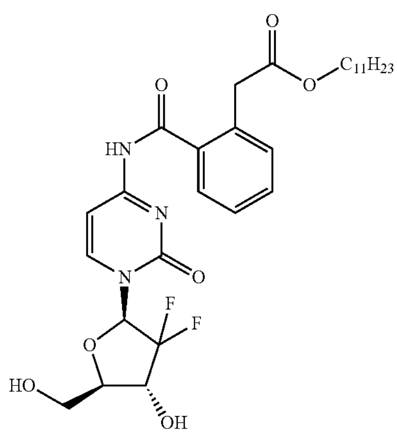 | LC (UV254) purity 90%. LC-MS m/z 580 [M + H]+ |
| NO. 33 | Undecyl 2-(2-(1-((2R,4R,5R)-3,3-difluoro-4-hydroxy-5-(hydroxymethyl)-tetrahydrofuran-2-yl)-2-oxo-1,2-dihydropyrimidin-4-ylamino)-2-oxoethyl)benzoate | 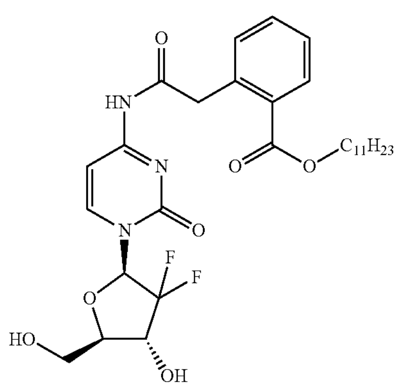 | LC (UV254) purity 90%. LC-MS m/z 580 [M + H]+ |

TABLE 1-continued

Structure and Characterization Data of the Compounds

| No. | Name | Structure | Data |
|---|---|---|---|
| NO. 34 | Dodecyl 2-(1-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)phenyl)acetate | 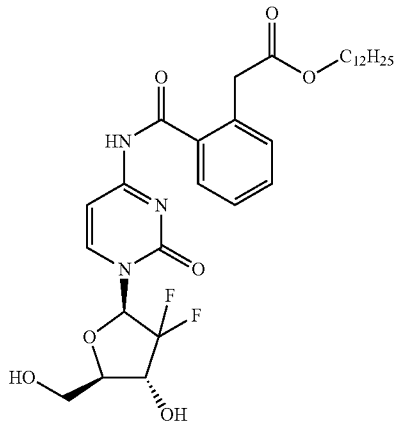 | LC (UV254) purity 93%. LC-MS m/z 594 [M + H]+ |
| NO. 35 | Dodecyl 2-(2-(1-((2R,4R,5R)-3,3-difluoro-4-hydroxy-5-(hydroxymethyl)-tetrahydrofuran-2-yl)-2-oxo-1,2-dihydropyrimidin-4-ylamino)-2-oxoethyl)benzoate | 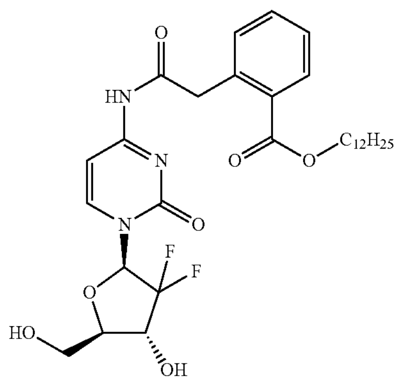 | LC (UV254) purity 93%. LC-MS m/z 594 [M + H]+ |
| NO. 36 | Undecyl 2-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)cyclohexanecarboxylate | 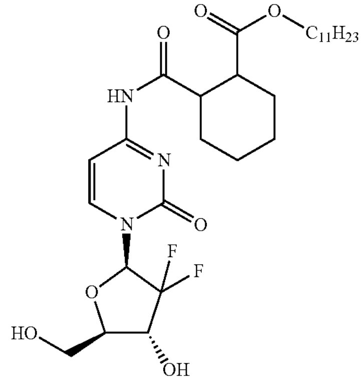 | LC (UV254) purity 95%. LC-MS m/z 572 [M + H]+ |

TABLE 1-continued

Structure and Characterization Data of the Compounds

| No. | Name | Structure | Data |
|---|---|---|---|
| NO. 37 | $N^2$-(1-((2R,4R,5R)-3,3-difluoro-4-hydroxy-5-(hydroxymethyl)-tetrahydrofuran-2-yl)-2-oxo-1,2-dihydropyrimidin-4-yl)-$N^3$-dodecylpyrazine-2,3-dicarboxamide | 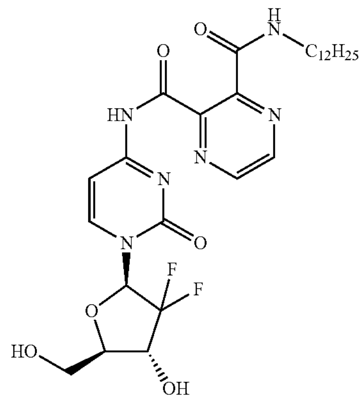 | LC (UV254) purity 97%. LC-MS m/z 581 [M + H]$^+$ $^1$HNMR (DMSO, 600 MHz) δ = 0.85 (t, 3H), 1.23-1.25 (m, 18H), 1.49 (m, 2H), 3.22 (m, 2H), 3.66 (m, 1H), 3.83 (m, 1H), 3.91 (d, 1H), 4.22 (m, 1H), 5.34 (t, 1H), 6.17 (s, 1H), 6.34 (d, 1H), 7.40 (brs, 1H), 8.33 (d, 1H), 8.83 (dd, 2H), 8.99 (m, 1H), 11.40 (S, 1H). |
| NO. 38 | Dodecyl 6-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)pyridazine-3-carboxylate | 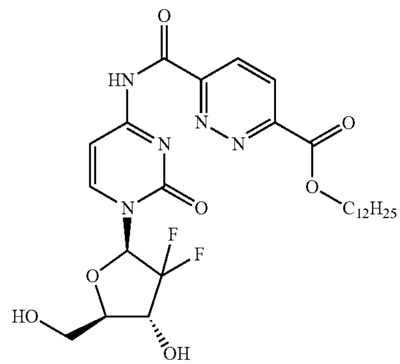 | LC (UV254) purity 95%. LC-MS m/z 582 [M + H]$^+$ |
| NO. 39 | Dodecyl 6-((1-((2R,4R,5R)-3,3-difluoro-4-hydroxy-5-(hydroxymethyl)-tetrahydrofuran-2-yl)-2-oxo-1,2-dihydropyrimidin-4-yl)carbamoyl)pyrimidine-4-carboxylate | 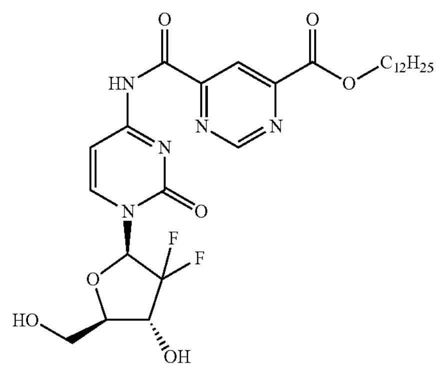 | LC (UV254) purity 96%. LC-MS m/z 582 [M + H]$^+$ |

Pharmacology Test

Cell analytical methods:

MTT analytical method was used to test the prodrugs for various tumor cells.

Materials

1) Cell lines: NCI-H460, A549, LOVO, HT-29, MDA-MB-231, SGC7901, HepG2 or BEL-7402 cell lines. Culture: adherent culturing in D-MEM (Hyclone, Inc.) containing 10% fetal calf serum. The initial cell concentration was about 3×10$^5$ /mL. The cell was passaged by 1:3 dilution in every 2-3 days. On the day before the test, the cell was passaged by 1:2 dilution, the cell concentration for the test was 5-10×10$^5$ /mL.
2) Dissolution and dilution of compounds: according to the weight and molecular weight of the drugs provided, 100-200 μL of DMSO was added. Then normal saline was added to make the final diluted concentration of the drugs be 5 mM (Note that the final concentration of DMSO should not be more than 10%).
3) D-MEM or RPMI 1640 cell culture medium, Gibco, Inc.
4) Fetal calf serum Hyclone, Inc.
5) Cell dissociation buffer, 0.25% Trypsin+0.02% EDTA.
6) MTT solution, MTT Powder (Sigma) were dissolved in PBS buffer solution to make a solution of 5 mg/mL. The solution was filtered by a 0.22 μm micropore membrane and stored at −20° C.
7) PBS buffer solution.
8) 10% acidified SDS, 0.01N HCl.
9) Centrifuge tubes, haustorial tubes etc. (BD, Inc.); 96-well plates (Costatr, Inc.)

Procedures:

1) Cell inoculation: Cells grown for 24 hours after passage, which cells were in good growth state, were used. The cells were harvested by the routine method. The cell concentration was adjust with a fresh culture solution to $2\times10^5$/mL (for adherent cells)-$3\times10^5$/mL (for suspension cells). The adherent cells were inoculated at 100 µL/well and then cultivated in an incubator with 5% $CO_2$ at 37° C. for 24 h. Thereafter the used culture solution was removed and 95 µL/well of fresh culture solution was added. The suspension cells were inoculated at 95 µL/well directly.

2) Drugs treatment: 9 concentration grades were designed for every drug, and every concentration had 3 wells. The control group had 5 wells. The control group was tested simultaneously in each test. The final concentrations of a drug added were 0.25, 0.125, 0.0625, 0.03125, 0.016, 0.008, 0.004, 0.002 mM, and 5 µL normal saline was added to the control group.
3) Cell culture and detection: the cells were cultured in an incubator with 5% $CO_2$ at 37° C. for 72 h after the drug was added, then 10 µL MTT was added to each well and the culture was continued for 4 h. 100 µL of 10% SDS (containing 0.01N HCl) was added to each well. After 24 h, the absorbance (A) of each well was determined by Bio-rad 680 ELISA with the detection wavelength of 570 nm and the reference wavelength of 630 nm.

Calculation:

First, the absorbance (A) of each well was averaged (removing any data with big difference). The inhibition rate (IR) for each cell line at each drug concentration was calculated according to the following formula:

$$IR\% = (1 - A_n/A_0) \times 100\%$$

Wherein $A_n$ was the mean absorbance of the test wells. $A_0$ was the mean absorbance of the control wells. The effect curve of the drug concentration was drawn using EXCEL software and the drug concentration for 50% cell survival was calculated according to an appropriate computing methods.

TABLE 2

$IC_{50}$ (mM) of Compounds for Eight Human Cell Lines

| Compound | A549 | NCI-H460 | HT29 | LOVO | Bel7402 | HepG2 | SGC7901 | MDA-MB-231 |
|---|---|---|---|---|---|---|---|---|
| 1 | 0.023 | | 0.013 | | 0.02 | | | |
| 2 | b | | a | | 0.162 | | | |
| 3 | b | | 0.01 | | 0.06 | | | |
| 4 | <0.002 | <0.002 | 0.002 | 0.016 | 0.008 | 0.006 | >0.016 | >0.016 |
| 5 | b | <0.002 | 0.03 | 0.001 | 0.016 | 0.004 | >0.016 | >0.016 |
| 6 | b | | 0.013 | | 0.03 | | | |
| 7 | b | | 0.08 | | 0.125 | | | |
| 8 | 0.004 | <0.002 | 0.006 | 0.014 | 0.023 | 0.007 | >0.016 | >0.016 |
| 9 | 0.004 | <0.002 | 0.003 | 0.005 | 0.013 | 0.006 | >0.016 | >0.016 |
| 10 | 0.013 | | 0.004 | | 0.03 | | | |
| 11 | 0.003 | | <0.002 | | 0.004 | | | |
| 12 | b | | 0.02 | | 0.06 | | | |
| 14 | 0.14 | | 0.035 | | a | | | |
| 15 | 0.003 | <0.001 | <0.002 | 0.016 | 0.004 | 0.004 | >0.016 | 0.011 |
| 18 | 0.015 | | 0.007 | | 0.016 | | | |
| 19 | b | | 0.025 | | 0.046 | | | |
| 20 | 0.013 | | 0.006 | | 0.014 | | | |
| 21 | b | | 0.024 | | 0.043 | | | |
| 22 | 0.008 | | 0.03 | | 0.016 | | | |
| 24 | 0.008 | | 0.008 | | 0.016 | | | |
| 26 | 0.003 | <0.001 | 0.002 | 0.016 | 0.008 | 0.002 | >0.016 | 0.006 |
| 27 | 0.004 | <0.001 | <0.002 | 0.002 | 0.004 | 0.001 | >0.016 | <0.001 |
| 28 | 0.008 | | 0.002 | | 0.008 | | | |
| 29 | 0.003 | | <0.002 | | 0.008 | | | |
| 30 | 0.014 | | 0.004 | | 0.016 | | | |
| 31 | 0.021 | | 0.007 | | 0.03 | | | |
| 36 | b | | a | | a | | | |
| Gem | <0.002 | <0.001 | 0.007 | <0.001 | 0.004 | <0.001 | >0.016 | <0.001 | a: $IC_{50}$ > 0.2 mM
b: not tested
Gem: gemcitabine as control
A549: a human lung cancer cell line
NCI-H460: a human lung cancer cell line
HT29: a human colon cancer cell line
LOVO: a human colon cancer cell line
Bel7402: a human liver cancer cell line
HepG2: a human liver cancer cell line
SGC7901: a human gastric cancer line
MDA-MB-231: a human breast cancer line Pharmacokinetics Test
1. Experimental Material
1.1 Instruments CX-250 ultrasound cleaner (Beijing Second Medical Equipment Factory); LC-10ATVP-ODS HPLC (Shimadzu, Japan); SPD-10A VP UV detector (Shimadzu, Japan); 80-2 type centrifuge (Guohua Instruments Inc. Ltd.); TGL-16G-A high speed refrigerated centrifuge (Shanghai Anting Scientific Instrument Factory); GL-8813 vortex mixer (Jiangsu Haimen Qilin Medical Instrument Factory).

1.2 Animals

Kunming strain white mice (25+1 g, provided by Experimental Animal Center of Shandong University, half of which were male, half were female).

2. Methods and Results
1. Evaluation of In Vitro Physiological Stability
    1.1 Evaluation of In Vitro Stability of Gemcitabine and its Two Prodrugs in Simulated Intestinal Fluid Gemcitabine and its two prodrugs were dissolved in the simulated intestinal fluid and was sampled at 0, 1, 2, 4, 6, 8, 12, 24 h, respectively. The drug concentrations were determined by HPLC test method to measure the stability of the gemcitabine and the two prodrugs in the simulated intestinal fluid. The results are listed in Table 3.

TABLE 3

In Vitro Stability of Gemcitabine, SL-01 and SL-02 in Simulated Intestinal Fluid

| | Simulated Intestinal Fluid | | | |
|---|---|---|---|---|
| Time | Gemcitabine | Degrade % | SL-01 | SL-02 |
| 0 min | 643704.938 | 0 | 288987.906 | 251093.500 |
| 1 h | 465528.594 | 27.67 | 231129.797 | 246642.203 |
| 2 h | 410685.313 | 36.2 | 196319.828 | 260214.703 |
| 4 h | 257604.125 | 59.98 | 245622.906 | 262169.906 |
| 6 h | 197106.406 | 69.37 | 247957.219 | 266558.938 |
| 8 h | 149816.906 | 76.72 | 239958.297 | 272841.656 |
| 12 h | 9873.897 | 98.46 | 247782.500 | 250558.797 |
| 24 h | 5571.352 | 99.13 | 256782.600 | 240246.594 |

Results: as shown in the above table, gemcitabine was degraded while SL-01 and SL-02 were stable in the simulated intestinal fluid.

1.2 Evaluation of Physiological Stability in PBS (pH=7.4)

Gemcitabine and its two prodrugs were dissolved in PBS (pH=7.4) and was sampled at 0, 1, 2, 4, 6, 8, 12, 24 h, respectively. The drug concentration was determined by HPLC test method to measure the stability of gemcitabine in PBS buffer (pH=7.4). The results are listed in Table 4.

TABLE 4

In Vitro Stability of Gemcitabine, SL-01 and SL-02 in PBS (pH 7.4)

| | PBS(pH = 7.4) | | |
|---|---|---|---|
| Time | Gemcitabine | SL-01 | SL-02 |
| 0 min | 657583.875 | 399795.688 | 289882.063 |
| 1 h | 646932.375 | 379856.688 | 274649.094 |
| 2 h | 651326.375 | 397725 | 284440.094 |
| 4 h | 647537.813 | 373725.406 | 284744.625 |
| 6 h | 618724 | 360109.813 | 299753.813 |
| 8 h | 635026.875 | 362068.688 | 282661.406 |
| 12 h | 600425.125 | 386125.688 | 297430.75 |
| 24 h | 603669.813 | 387541.688 | 290547 |

Results: As shown in the above table, gemcitabine, SL-01 and SL-02 were stable in PBS (pH=7.4).

2. Stability of Gemcitabine and its Two Prodrugs in Blood Plasma 2.1 Treatment of Plasma Samples 200 μL of plasma samples was transferred into a EDTA-treated tube containing 2.5 μL tetrahydrouridine solution (THU, 10 mg/ml, a cytidine deaminase inhibitor which can prevent gemcitabine from metabolizing to deoxyuridine). Isopropanol (1 mL) was then added into the blood sample and vortexed for 30 s and kept still for 5 min. 2.5 ml of EtOAc was added and votexed and centrifuged at 4000 rpm for 15 minutes. The supernatant was taken and dried by blowing in nitrogen. The dried sample was redissolved in 200 μL HPLC mobile phase solution. 20 μL sample was loaded to the HPLC.

2.2 Stability of Gemcitabine and its Prodrugs in Human Blood Plasma

The standard solutions of gemcitabine, SL-01 and SL-02 were diluted in plasma respectively and sampled at 0, 1, 2, 4, 6, 8, 12, 24 h, respectively. The samples were processed using the standard method. 20 μL samples were loaded and the chromatography peak areas were recorded and used to measure the drug concentrations and investigate the stability of gemcitabine, SL-01 and SL-02 in the plasma. The results are shown in Table 5.

TABLE 5

Stability Test of Gemcitabine, SL-01 and SL-02 in Blood Plasma

| | Plasma | | | | |
|---|---|---|---|---|---|
| Time | Gemcitabine | SL-01 | Degrade % | SL-02 | Degrade % |
| 0 min | 562562.938 | 336275.344 | 0 | 260988.766 | 0 |
| 1 h | 592859.625 | 326948.219 | 2.77 | 231176.578 | 11.42 |
| 2 h | 466418.094 | 261917.094 | 22.11 | 188092.719 | 27.93 |
| 4 h | 483743.594 | 178242.781 | 46.99 | 139849.094 | 46.42 |
| 6 h | 552648.313 | 59465.750 | 82.31 | 87365.656 | 66.53 |
| 8 h | 540059.125 | 43894.633 | 89.64 | 84379.297 | 67.67 |
| 12 h | 544300.688 | 12894.514 | 96.17 | 44450.098 | 82.97 |

Results: as shown in the above table, gemcitabine was stable in blood plasma, but SL-01 and SL-02 were degradable in blood plasma.

3 Animal Experiment 3.1 Gemcitabine

A suitable amount of gemcitabine was weighed to prepare the control solution containing 6.25 mg/mL gemcitabine. The solution was filtered and sterilized using a 0.22 μm microfiltration membrane.

120 healthy Kunming mice were taken and divided into two groups randomly. The first group was given gemcitabine by oral administration (intragastric administration). The second group was given gemcitabine by intravenous injection in a tail vein. Five mice were settled parallel at each time point. The dosage was 50 mg/kg (equivalent to 0.2 mL per mouse). The mice were fasted but allowed to drink for a 12 h period before administration. Blood samples were drawn from eye-base veniplex at 5 min, 15 min, 30 min, 45 min, 1 h, 2 h, 4 h, 6 h, 8 h, 12 h, 24 h, 48 h after the administration and put into hepain sodium treated centrifuge tubes containing 2.5 μL tetrahydrouridine solution (THU, 10 mg/ml) and centrifuged for 15 min at 4000 r/min. Isopropanol (1 mL) was added into the solution and vortexed for 30 s and kept still for 5 min. 2.5 ml of EtOAc was added and votexed and centrifuged at 4000 rpm for 15 minutes. The supernatant was taken and dried by blowing in nitrogen. The dried sample was redissolved in 200

µL HPLC mobile phase solution. 20 µL sample was loaded to the HPLC. The chromatography and peak area were recorded. The plasma concentration of gemcitabine was calculated. The average concentration of gemcitabine was plotted with the time. These results are shown in Table 6.

TABLE 6

Pharmacokinetic Parameters of Gemcitabine

| Parameters | Intravenous Administration Group | Oral Administration Group |
|---|---|---|
| $C_{max}$ (µg/mL) | 11.54 | 2.60 |
| $MRT_{0-t}$ (h) | 1.07 | 1.28 |
| $T_{1/2}$ (h) | 0.97 | 0.83 |
| $T_{max}$ (h) | 0.083 | 0.50 |
| $AUC_{0-t}$ (µg/ml * h) | 11.30 | 4.02 |
| Absolute bioavailability | 35.57% | |

Note:
Absolute bioavailability = $AUC_{oral}/AUC_{iv}$

3.2 Pharmacokinetics of SL-01 and SL-02

125 mg of SL-01 or SL-02 were weighed accurately and added into 10 mL volumetric flask. Water (containing 0.1% Tween-80) was added to the mark and mixed uniformly to get the suspensions of SL-01 or SL-02.

100 healthy Kunming mice were taken and divided into two groups randomly. The first group was given SL-01 and the second group was given SL-02. Five mice were settled parallel at each time point. SL-01 and SL-02 were administrated intragastricly with a dosage at 100 mg/kg (equivalent to 0.2 mL per mouse). The mice were fasted but allowed to drink for a 12 h period before administration. Blood samples were drawn from eyebase veniplex at 5 min, 15 min, 30 min, 45 min, 1 h, 2 h, 4 h, 6 h, 8 h, 12 h, 24 h, 48 h after the administration and put into heparin sodium treated centrifuge tubes containing 2.5 µL tetrahydrouridine solution (THU, 10 mg/ml) and centrifuged for 15 min at 4000 r/min. Isopropanol (1 mL) was added into the solution and vortexed for 30 s and kept still for 5 min. 2.5 ml of EtOAc was added and votexed and centrifuged at 4000 rpm for 15 minutes. The supernatant was taken and dried by blowing in nitrogen. The dried sample was redissolved in 200 µL HPLC mobile phase solution. 20 µL sample was loaded to the HPLC. The chromatography and peak area was recorded. The plasma concentrations of SL-01 and SL-02 was calculated. The average concentration of SL-01 and SL-02 was plotted with the time. These results are shown in Tables 7 and 8.

TABLE 7

Pharmacokinetic Parameters of SL-01

| Parameters | SL-01 Administration Group | Gemcitabine Produced in SL-01 | Sum of SL-01 Degradation and Gemcitabine Production |
|---|---|---|---|
| $C_{max}$ (µg/ml) | 4.37 | 4.48 | 6.82 |
| $MRT_{0-t}$ (h) | 0.36 | 3.43 | 2.51 |
| $T_{1/2}$ (h) | 0.519 | 8.67 | 8.671 |
| $T_{max}$ (h) | 0.250 | 0.083 | 0.083 |
| $AUC_{0-t}$ (µg/ml * h) | 1.81 | 5.28 | 7.65 |

TABLE 7-continued

Pharmacokinetic Parameters of SL-01

| Parameters | SL-01 Administration Group | Gemcitabine Produced in SL-01 | Sum of SL-01 Degradation and Gemcitabine Production |
|---|---|---|---|
| Absolute bioavailability of SL-01 versus gemcitabine | | | 33.8% |
| Relative bioavailability of SL-01 versus gemcitabine | | | 95.15% |

Note:
Absolute bioavailability of SL-01 versus gemcitabine = $AUC_{sum\ of\ Degradation\ and\ Gemcitabine\ Production\ by\ SL-01} \times D_{gemcitabine-iv}/(AUC_{gemcitabine-iv} \times D_{SL-01})$
Relative bioavailability of SL-01 versus gemcitabine = $AUC_{sum\ of\ Degradation\ and\ Gemcitabine\ Production\ by\ SL-01} \times D_{oral-gemcitabine}/(AUC_{oral-gemcitabine} \times D_{SL-01})$
D: Dosage;

TABLE 8

Pharmacokinetic Parameters of SL-02

| Parameters | Gemcitabine produced in SL-02 |
|---|---|
| $C_{max}$ (µg/ml) | 1.29 |
| $MRT_{0-t}$ (h) | 2.08 |
| $T_{1/2}$ (h) | 2.73 |
| $T_{max}$ (h) | 0.083 |
| $AUC_{0-t}$ (µg/ml * h) | 2.73 |
| Absolute bioavailability of SL-02 versus gemcitabine | 12.07% |
| Relative bioavailability of SL-02 versus gemcitabine | 33.9% |

Note:
Absolute bioavailability of SL-02 versus gemcitabine = $AUC_{sum\ of\ Degradation\ and\ Gemcitabine\ Production\ by\ SL-02} \times D_{gemcitabine-iv}/(AUC_{gemcitabine-iv} \times D_{SL-02})$
Relative bioavailability of SL-02 versus gemcitabine = $AUC_{sum\ of\ Degradation\ and\ Gemcitabine\ Production\ by\ SL-02} \times D_{gemcitabine-oral}/(AUC_{gemcitabine-oral} \times D_{SL-02})$
D: Dosage;

4 Metabolism of Gemcitabine, SL-01, SL-02 in Liver Microsomal Enzymes

4.1 Preparation of Liver S9

The liver of a mouse was taken out and washed by cold normal saline and dried with filter paper, then cut into small pieces. They were washed 2-3 times with ice cold PBS (pH=7.4) until the elute became colorless or faint yellow. The small pieces of the liver were cut into fragments. Then PBS (pH=7.4) solution in an amount four times of the weight of the liver was added. The liver fragments were homogenated under ice-bath to avoid the down-regulation of enzymatic activity. The homogenated mixture was transferred into a centrifuge tube with stopper and centrifuged for 20 min at 4000 r/min to get the supernatant. Then, the supernatant was centrifuged at 12000 r/min for 20 min to get the supernatant, which was the S9 fraction.

4.2 Metabolic Studies On Enzyme

Liver microsomal S9 was mixed with drug solutions. 1800 µL of the mixture in test tube was pre-incubated in a water-bath for 5 min at 37° C. 200 µL of 10 mmol/L NADPH solution was added to start the reaction. The final reaction volume was 2 mL. 200 µL of the incubation solution was taken at 0 min, 10 min, 20 min, 40 min, 1 h, 2 h, 4 h, 6 h, 12 h, respectively. 1 mL of ice cold isopropanol was added into the solution immediately and vortexed for 30 s and kept still for 5 min. 2.5 mL of EtOAc was added and vortexed and centrifuged at 4000 rpm for 15 min. The supernatant was taken and dried by blowing in nitrogen. The dried sample was redissolved in 200 µL HPLC mobile phase solution. 20 µL sample was loaded to the HPLC. The chromatography and peak area were recorded. The results are shown in Table 9.

TABLE 9

Metabolism of Gemcitabine, SL-01, SL-02 in Liver Microsomal Enzymes

| | Degradation in liver S9 Fraction | | | | | |
|---|---|---|---|---|---|---|
| Time | Gemcitabine, | Degrade % | SL-01, | Degrade % | SL-02, | Degrade % |
| 0 min | 104493.3 | 0 | 179613.3 | 0 | 197862.4 | 0 |
| 1 h | 100684.3 | 3.64 | 172893.5 | 3.74 | 111791.7 | 43.50 |
| 2 h | 45804.8 | 56.16 | 142419.3 | 20.71 | 80866.7 | 59.13 |
| 4 h | 29235.3 | 72.02 | 64632.59 | 64.02 | 99798.8 | 49.56 |
| 6 h | 15103.03 | 85.55 | 27009.4 | 84.96 | 43707.2 | 77.91 |
| 12 h | 5092.7 | 95.13 | 18730.51 | 89.57 | 17514.94 | 91.15 |

Animal Experiments of Inhibition of Cancer Cell Growth by Intravenous Administration of SL-01

1. Dissolution and dilution of compounds: 506.6 mg of gemcitabine hydrochloride or 482.4 mg of SL-01 powder was dissolved in normal saline and DMSO (Sigma), respectively. The highest concentrations of both were 10 mg/mL and 240 mg/mL, respectively. The drugs were diluted with Grephor EL, EtOH and normal saline, as shown in detail in Table 10. Assuming that each mouse weighed 20 g and 0.1 mL of drug solution was administered, then the dosage of SL-01 at 5, 10 or 20 mg/kg needed drug concentrations of 1, 2, 4 mg/mL, respectively. The drugs were packaged and stored at −20° C.

TABLE 10

| Group | Dosage (mg/mL) | Grephor EL (mL) | EtOH (mL) | SL-01 (240 mg/mL) | Normal Saline (mL) | Drug concentration in DMSO (%) | Drug concentration in EtOH (%) |
|---|---|---|---|---|---|---|---|
| SL-01 | 4 | 1.25 | 1.25 | 168 µL | 7.33 | 1.7 | 12.5 |
| | 2 | 1.25 | 1.25 | 84 µL | 7.42 | 0.85 | 12.5 |
| | 1 | 1.25 | 1.25 | 42 µL | 7.46 | 0.42 | 12.5 |
| Control | 0 | 1.25 | 1.25 | DMSO: 84 µL | 7.42 | 0.85 | 12.5 |
| Gem | 2 | 1.25 | 1.25 | 2 mL (From GEM solution, 10 mg/mL) DMSO: 84 µL | 5.42 | 0.85 | 12.5 |

2. Cell lines and cultivation: the NCI-H460 lung cancer cell line, the HepG2 liver cancer cell line, or the HT29 colon cancer cell line were cultured by adherent culturing in D-MEM (Gibco, Inc.) containing 10% fetal calf serum. These cells were passaged once by a dilution of 1:3 in every 2-3 days. The cells were collected when they were passaged to grow into 25 of 10 cm culture dishes.

3. Experimental Method:

3.1 The establishment of a model of transplanted tumors in nude mice: Well-grown NCI-H460 cells, HT29 cells or HepG2 cells were collected (25 of 10 cm culture dishes). The cell concentration was adjusted to $1.5 \times 10^7$/mL with serum-free DMEM. 200 µL cell suspension was inoculated into the right back of 6 weeks old male BALB/C nude mice by subcutaneous injection using a 1 mL syringe.

3.2 Animal groups and treatment: these nude mice were randomly divided into 5 groups with 3-4 mice for each group when the tumor volume grew 300 mm$^3$: (1) control group, (2) gemcitabine positive control group (GEM) (10 mg/Kg), (3) SL-01 low dosage group (5 mg/Kg), (4) SL-01 middle dosage group (10 mg/Kg), and (5) SL-01 high dosage group (20 mg/Kg). The treatment starting day was the first day ($d_0$). The corresponding drugs were injected intravenously to the tail vein every three days. The administration volume to each mouse was adjusted according to its body weight. A total of four administrations (d0, d3, d6, d9) were applied. The long and short tumor pathlines were measured with a slide caliper at the beginning of the administration and every 3 days thereafter. The tumor volume V was calculated ($V=\frac{1}{2}ab^2$, a is the tumor long pathline, b is the tumor short pathline). The growth curve was drawn with the time as the horizontal axis, and tumor volume as the vertical axis. The experiment was terminated when the tumor size of the control group reached 3000 mm$^3$. Blood samples were taken from the eyeball and thereafter the nude mice were euthanized by back neck vertebra cervical dislocation. The tumor tissues were removed and weighed. The inhibition rate of tumor growth was calculated. The inhibition rate of tumor growth (%)=(1−average tumor weight of treatment group/average tumor weight of control group)×100%.

4. Experimental Results:

4.1 According to the tumor growth curve and tumor weight, both SL-01 and gemcitabine have inhibitory effect on the NCI-H460 tumor transplanted in nude mice. Comparing to gemcitabine, SL-01 has a little weaker inhibitory effect. The high dose group (20 mg/kg) of SL01 has similar inhibitory effect as GEM (10 mg/Kg). Judging the drug toxicity by the weight loss, however, the weight loss rate of gemcitabine positive control was 14% while that of SL-01 with high dose group (20 mg/Kg) was 7% only, which indicated SL01 had a lower toxicity.

4.2 The low, middle and high dosage of SL-01 in the treatment for HepG2 liver cancer cell line tumor growth transplanted in nude mice are 10, 20 and 40 mg/kg, respectively. Judging from tumor growth curve and tumor weight, neither SL-01 nor gemcitabine has shown an obvious inhibitory effect on the growth of HepG2 tumor transplanted in nude mice. The high dosage group of SL01 (40 mg/kg) has similar inhibitory rate as the Gem group. Judging the drug toxicity by body weight loss, the weight loss rate of the gemcitabine positive control was 9%, and that of the low dosage, middle dosage and high dosage groups of SL-01 were 11.6%, 14% and 3.5%, respectively.

4.3 Judging from the tumor growth curve made from the relative volumes, the Gem group and the middle dosage group (20 mg/kg) and the high dosage group (40 mg/kg) of SL01 have certain inhibitory effect on the growth of HT29 tumor transplanted in nude mice The inhibitory rate was 15%, 23% and 7%, respectively, at the end of the experiments. SL-01 had better inhibitory effect than the Gem group at the same dosage. Judging the drug toxicity by body weight loss, neither the gemcitabine positive control group nor SL-01 has obvious toxicity. The weight loss rate of the Gem group (20 mg/kg) and the SL-01 (20 mg/kg) group at the same dosage was 4% and 8% at d17, respectively.

Animal Experiments of Cancer Cell Inhibition with Oral Administration of SL-01

1. Experimental Material

1. SL-01 is a white power and cannot be dissolved in water well. Suspension formulation was prepared using 2.5% starch for intragastric administration. Gemcitabine is a white power and can be easily dissolved in water. In the test, it was dissolved in normal saline and filtered with microfiltration membrane and administrated by tail vein injection. Positive control drug: Ftorafur (FT-207) produced by Qilu Pharmaceutical Co. Ltd., oral formulation.

2. Experimental animals: 50 Balb/c female nude mice at 4-5 weeks old, purchased from Peking University Health Science Center.

3. Tumor cells, culture medium and various solutions:

H460 cells, a human lung cancer cell line were purchased from Shanghai Cell Bank of Chinese Academy of Sciences RPMI-1640 culture medium was purchased from Invitrogen, U.S. Fetal calf serum was purchased from Lanzhou National Hyclone Bio-engineering Co.

Other reagents include 0.02% EDTA-0.25% pancreatinum solution, PBS, normal saline.

4. Laboratory equipments include cell incubator, laminar flow cabinet, centrifuge, rat/mouse laminar flow table, vernier caliper, surgical equipment, syringe, gavage injection, automatic autoclave etc.

2. Experimental Method

1. Culture of tumor cells: H460 cells were cultured in an incubator with 5% $CO_2$ at 37° C. using RPMI-1640 nutrient solution containing 10% fetal calf serum. The cells were passaged through routine method.

2.2 Method of inoculating tumor cells in nude mice: cells were collected when they grew to about 80 bottles in culture flasks. Cells were washed twice with PBS before they were digested, then 1.5 mL of digestion solution juices was added into every bottle. They were observed under a microscope and the digestion was terminated after the cells were shed. Cell suspension was collected into 50 mL of centrifugal tube and centrifuged and washed twice with PBS. It was counted and suspended with 10 mL of normal saline to get the tumor cell suspension of inoculated nude mice. The tumor cells ($1 \times 10^7$/0.2 mL) were inoculated in the left front armpits of mice. The tumor growth was observed after the inoculation.

3. Experiment design, administration method and dosage adjustment instruction: the nude mice were randomly divided into five groups with 6 mice in each group 5 days after the inoculation: (1) negative control group with 6 mice, (2) positive control group with 6 mice, (3) SL-01 middle dosage group with 6 mice, (4) SL-01 low dosage group with 6 mice, and (5) gemcitabine control group with 6 mice.

TABLE 11

Dosage Regimens for Treating Nude Mice with SL-01

| Group | Number of Animals | Dosage | Administration Times/day | Administration Route |
|---|---|---|---|---|
| Negative control (distilled water) | 6 | 0.2 mL/mouse | 1 per 3 days | Gastric gavage |
| Ftorafur 120 mg/kg | 6 | 0.2 mL/mouse | 1 × 14 times | Gastric gavage |
| SL-01 middle dosage 60 mg/kg | 6 | 0.2 mL/mouse | 1 per 3 days | Gastric gavage |
| SL-01 low dosage 30 mg/kg | 6 | 0.2 mL/mouse | 1 per 3 days | Gastric gavage |
| Gemcitabine 30 mg/kg | 6 | 0.2 mL/mouse | 1 per 3 days | Intravenous injection |

4. Evaluation protocols for drug treating effect: these mice were weighed before drug administration and every week thereafter. The long tumor pathline (a) and the short tumor pathline (b) were measured at the same time. The formula for calculating the tumor volume is $V=(a \times b^2)/2$. Mice were euthanized after drug administration for 3 weeks. The tumor was taken out and weighed. The formula for calculating the inhibition rate of drug on tumor is inhibition rate %=($W_0$−W)/$W_0 \times 100\%$, wherein, $W_0$ was the tumor weight of the negative control group. W was the tumor weight of the treatment group.

3. Experimental result: the experimental period was 30 days of which 22 days was administration days and 7 administrations were given. The results were shown as follows:

1. The effect of the drugs on the tumor volume: the tumor volume of the nude mice in every group were measured at 7, 14, 18, 22 days after the administration. The results are shown in Table 12.

TABLE 12

Mean Volume of Nude Mice Tumor at Different Point of Time

| Measuring Time (Day) | Mean Volume of Tumor (mm³) | | | | |
|---|---|---|---|---|---|
| | Negative Control Group | Gemcitabine Control Group | FT-207 Control Group | SL-01 Middle Dosage Group | SL-01 Small Dosage group |
| 7 | 799.8 | 700.7 | 756.7 | 739.6 | 761.3 |
| 14 | 1259.3 | 759.7 | 1347.0 | 823.4 | 840.9 |
| 18 | 1505.9 | 804.5 | 1526.3 | 870.2 | 950.5 |
| 22 | 1727.1 | 868.0 | 1779.4 | 905.3 | 1092.0 |

2. Effect of the drugs on the weight of nude mice: gemcitabine intravenous injection group, SL-01 middle dosage group and SL-01 small dosage group have obvious effect on reducing the animal weight. As shown in Table 13, the weight of gemcitabine treatment group dropped 20.9%. The weight of SL-01 middle dosage group and SL-01 small dosage group dropped 14.8% and 14.3%, respectively.

TABLE 13

Mean Weight of Nude Mice at Different Point of Time

| Measuring Time (Day) | Mean Weight of Nude Mice (g) | | | | |
|---|---|---|---|---|---|
| | Negative Control Group | Positive Control Group | Gemcitabine Group | SL-01 Middle Dosage Group | SL-01 Small Dosage group |
| 0 | 19.3 | 19.3 | 19.1 | 19.5 | 19.6 |
| 7 | 20.3 | 19.5 | 19.0 | 19.1 | 19.3 |
| 14 | 22.2 | 19.8 | 18.6 | 19.6 | 19.9 |
| 22 | 23.0 | 19.7 | 18.2 | 19.6 | 19.7 |

3. The effect of the drugs on the tumor weight: the animals were euthanized at the end of the experiment. The tumors were taken out and weighed. The results are shown in Table 14.

TABLE 14

Tumor Weigh of Nude Mice in Every Group at the End of the Experiment

| Nude Mice No. | Tumor Weight (g) | | | | |
| --- | --- | --- | --- | --- | --- |
| | Negative Control | Positive Control | Gemcit-abine Group | SL-01 Middle Dosage Group | SL-01 Small Dosage group |
| 1 | 2.36 | 1.82 | 1.56 | 1.82 | 1.41 |
| 2 | 1.89 | 1.61 | 1.2 | 1.5 | 1.82 |
| 3 | 1.76 | 1.45 | 0.4 | 0.51 | 1.25 |
| 4 | 2.1 | 1.01 | 0.61 | 0.88 | 0.8 |
| 5 | 2.32 | 0.76 | 0.7 | 0.41 | 0.45 |
| 6 | 1.92 | 0.92 | 0.88 | 0.6 | 0.63 |
| Average Value | 2.05 | 1.26 | 0.89 | 0.95 | 1.06 |
| Inhibition ratio | — | 38.5% | 56.6% | 53.7% | 48.3% |

Analyzed by the t-test, the positive control group, gemcitabine group, SL-01 middle dosage group and SL-01 small dosage group have shown significant efficacy.

The invention claimed is:

1. A prodrug based on the structure of gemcitabine, having the structure of Formula (I)

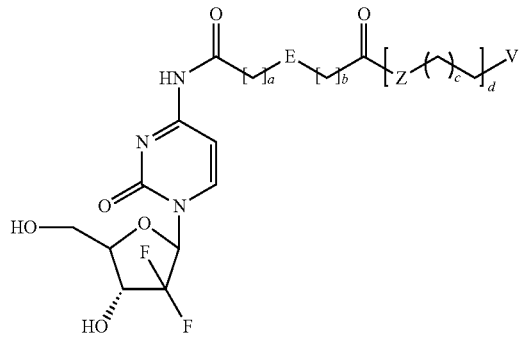

(I)

wherein a is an integer from 0 to 6; b is an integer from 0 to 6; c is an integer from 1 to 18; d is an integer from 1 to 4; E is a 5-member or 6-member cyclic hydrocarbonyl, 5-member or 6-member cycloalky with 1-4 heteroatoms, aryl, or hetero-aryl, the heteroatoms are selected from O, N or S;

Z is selected from O, N or S;

V is selected from hydrogen, hydrocarbonyl, alkoxyl, ester group, halogen, amide group, amino or substituted amino.

2. The prodrug based on the structure of gemcitabine of claim 1, wherein E is selected from any one of the following structures:

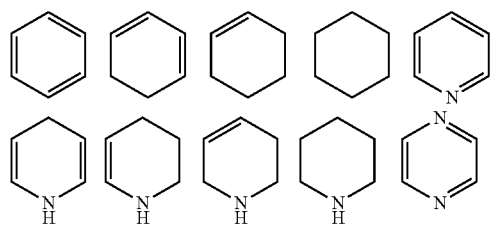

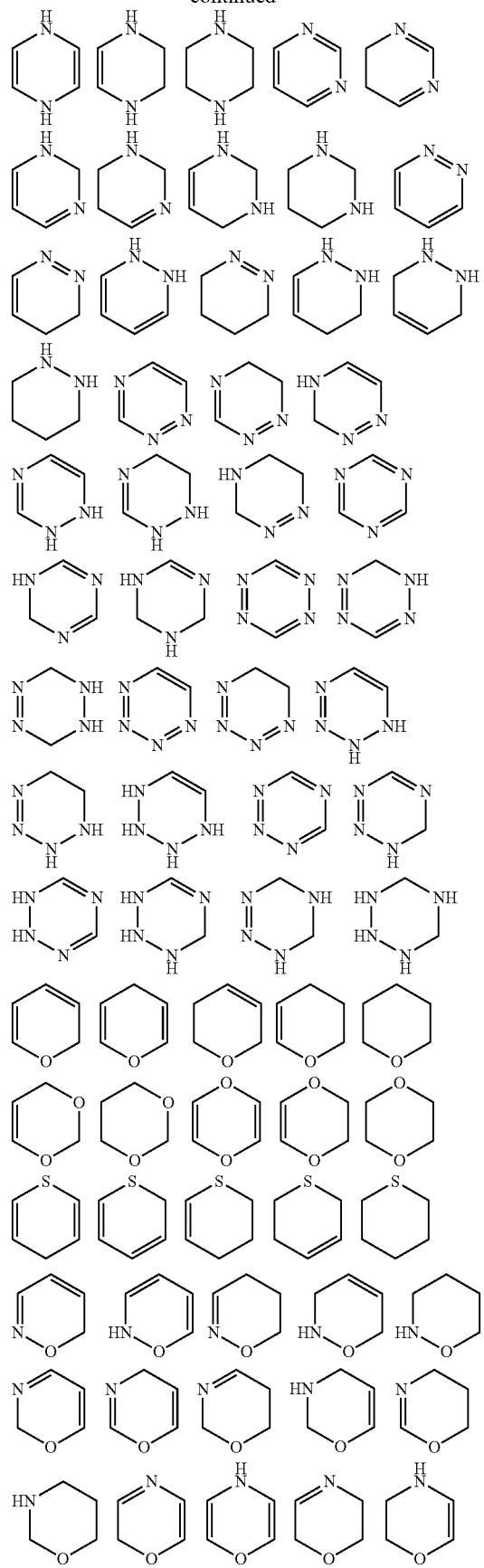

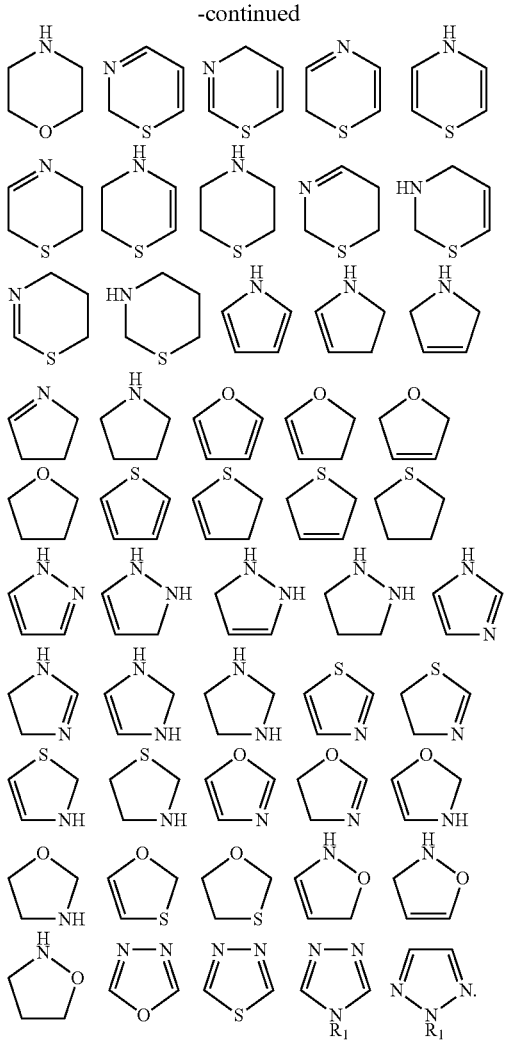

3. The prodrug based on the structure of gemcitabine of claim 2, wherein E is selected from any one of the following structures:

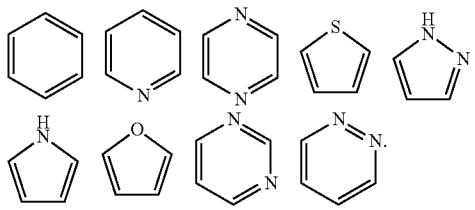

4. The prodrug based on the structure of gemcitabine of claim 1, wherein a is 0 or 1, b is 0 or 1, Z is O or N, c is 10-16, d is 1 or 2; V is selected from hydrogen or hydrocarbonyl groups.

5. A method for preparing the prodrug based on the structure of gemcitabine of claim 1, wherein be method comprises:

1) mixing acid anhydrides or acyl chlorides with alcohols or amines directly or as dissolved in organic solvents at the mole ratio of acid anhydride or acid chloride to alcohol or amine of 1:1-1:1.5 and reacting for 2-8 hours at a temperature ranging from room temperature to melting temperature to obtain the corresponding substituted adds;

2) dissolving gemcitabine hydrochloride, the substituted acids obtained from step 1), benzotriazole-1-yl-oxytripyrrolidinylphosphonium hexaflurophosphate and 4-dimethylaminopyridine in organic solvent at the mole ratio of gemcitabine hydrochloride, the substitutive acids obtained from step 1), benzotriazole-1-yl -oxytripyrrolidinylphosphonium hexaflurophosphate and 4-dimethylaminopyridine of 1:(1-2):(0.9-1.5):(1-3) and stirring for 12-24 h at room temperature;

3) adding the react on solution from step 2) into water, extracting ii, drying and purifying tie isolated organic phase to produce the desired product.

6. The method of preparing the prodrug based on the structure of gemcitabine of claim 5, wherein the acid anhydrides in step 1) are selected from phthalic anhydride, homophthalic anhydride, cyclohexane-1,2-dicarboxylic anhydride, cyclopentane-1,2-dicarboxylic anhydride, pyrazinedicarboxylic anhydride, pyridriedicarboxylic anhydride, thiophenedicarboxylic anhydride, furandicarboxylic anhydride, pyrroledicarboxylic anhydride, 1,2,3,6-tetrahydrophthalic anhydride.

7. The method of preparing the prodrug based on the structure of gemcitabine of claim 5, wherein the alcohols in step 1) are selected from n-octyl alcohol, n-nonyl alcohol, n-decyl alcohol, n-undecyl alcohol, lauryl alcohol, n-tetradecanol, n-hexadecanol, or n-octadecanol, wherein the amines in step 1) are selected from n-octylamine, n-nonylamine, n-decylamine, n-undecylamine, n-laurylaimine, n-tetradecylamine, n-hexadecylamine or n-octadecylamine.

8. The method of preparing the prodrug based on the structure of gemcitabine of claim 5, wherein the acyl chlorides in step 1) are obtained by the reaction of diacids with $SOCl_2$, $PCl_5$, $PCl_3$ or $POCl_3$, wherein the diacids are selected from pyrazine-2,3-dicarboxylic acid, pyridazine-3,6-dicarboxylic acid, isophthalic acid, pyrimidine-4,6-dicarboxylic acid, pyridine-2,5-dicarboxyic acid, pyridne-2, 3-dicarboxylic acid, pyridine-2,6-dicarboxylic acid, diphenyl-2,2'-dicarboxylic acid, thiophene-2,5-dicarboxylic acid, pyridine-3,4-dicarboxylic acid, pyridine-2,4-dicarboxylic add, pyrazole-3, 5-dicarboxylic acid, phthalic acid, terephthalic acid, thiophene-2,3-dicarboxylic acid, thiophene-3,4-dicarboxylic acid, thiophene-2,4-dicarboxylic add, pyrazole-3,4-dicarboxylic acid, cyclohexane-1,2-dicarboxylic acid, cyclohexane-1,3-dicarboxylic acid, cyclohexane-1,4-dicarboxylic acid, cyclopentane -1,2-dicarboxylic add, cyclopentane-1,3-dicarboxylic acid, cyclopentane-1,4-dicarboxylic add, pyrrole-2,3-dicarboxylic acid, pyrrole-2,4-dicarboxylic acid, pyrrole-2,5-dicarboxylic acid, furan2,3-dicarboxylic acid, furan-2,4dicarboxylic acid or furan-2,5-dicarboxylic acid.

9. The method of preparing the prodrug based on the structure of gemcitabine of claim 5, wherein the reaction time of step 1) is 3-4 h, in step 2), the gemcitabine hydrochloride, the substituted acid obtained from step 1), benzotriazole -1-yl-oxytripyrrolidinylphosphonium hexaflurophosphate and 4-dimethylaminopyridine (DMP) react at the mole ratio of 1:(1.1-1.3):(1.1-1.3):(1.1-1.3), the organic solvents in step 1) and 2) are selected from N,N-dimethylformamide, N,N-dimeyhylacetamide, tetrahydrofuran, dioxin, dimethyl sulfoxide, sulfolane or pyridne.

10. A method for treating lung cancer, pancreatic cancer, breast cancer, colon cancer, gastric cancer or liver cancer in a subject, comprising administering an effective amount of the prodrug based on the structure of gemcitabine of any of the claims 1-4 to the subject.

* * * * *